US010072072B2

(12) United States Patent
Vora et al.

(10) Patent No.: US 10,072,072 B2
(45) Date of Patent: Sep. 11, 2018

(54) ANTIBODY NEUTRALIZING HUMAN RESPIRATORY SYNCYTIAL VIRUS

(71) Applicant: Merck Sharp & Dohme Corp., Rahway, NJ (US)

(72) Inventors: Kalpit A. Vora, Yardley, PA (US); Kara S. Cox, Harleysville, PA (US); Aimin Tang, Lansdale, PA (US); Zhifeng Chen, Warrington, PA (US); Daniel DiStefano, Harleysville, PA (US); Lan Zhang, Chalfont, PA (US); Hua-Poo Su, Phoenixville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/928,566

(22) Filed: Mar. 22, 2018

(65) Prior Publication Data

US 2018/0215810 A1 Aug. 2, 2018

Related U.S. Application Data

(62) Division of application No. 15/335,560, filed on Oct. 27, 2016, now Pat. No. 9,963,500.

(60) Provisional application No. 62/367,359, filed on Jul. 27, 2016, provisional application No. 62/247,841, filed on Oct. 29, 2015.

(51) Int. Cl.
*A61K 39/00* (2006.01)
*A61K 39/155* (2006.01)
*C07K 16/10* (2006.01)
*A61K 39/42* (2006.01)
*C07K 14/005* (2006.01)

(52) U.S. Cl.
CPC .......... *C07K 16/1027* (2013.01); *A61K 39/42* (2013.01); *A61K 2039/505* (2013.01); *A61K 2039/54* (2013.01); *A61K 2039/545* (2013.01); *C07K 2317/14* (2013.01); *C07K 2317/21* (2013.01); *C07K 2317/34* (2013.01); *C07K 2317/41* (2013.01); *C07K 2317/524* (2013.01); *C07K 2317/565* (2013.01); *C07K 2317/732* (2013.01); *C07K 2317/76* (2013.01); *C07K 2317/92* (2013.01); *C07K 2317/94* (2013.01)

(58) Field of Classification Search
CPC .............. C07K 16/1027; C07K 14/005; C12N 2760/18534; A61K 39/155; A61K 2039/505
See application file for complete search history.

(56) References Cited

U.S. PATENT DOCUMENTS

| | | | |
|---|---|---|---|
| 5,624,821 A | 4/1997 | Winter et al. | |
| 5,648,260 A | 7/1997 | Winter et al. | |
| 5,677,425 A | 10/1997 | Bodmer et al. | |
| 5,714,350 A | 2/1998 | Sung et al. | |
| 5,762,905 A | 6/1998 | Burton et al. | |
| 5,811,524 A | 9/1998 | Brams et al. | |
| 5,842,307 A | 10/1998 | Johnson | |
| 5,840,298 A | 11/1998 | Brams et al. | |
| 5,866,125 A | 2/1999 | Brams et al. | |
| 5,869,046 A | 2/1999 | Presta et al. | |
| 5,939,068 A | 8/1999 | Brams et al. | |
| 5,955,364 A | 9/1999 | Brams et al. | |
| 5,958,765 A | 9/1999 | Brams et al. | |
| 6,121,022 A | 9/2000 | Presta et al. | |
| 6,194,551 B1 | 2/2001 | Idusogie et al. | |
| 6,277,375 B1 | 8/2001 | Ward | |
| 6,331,415 B1 | 12/2001 | Cabily et al. | |
| 6,350,861 B1 | 2/2002 | Sung et al. | |
| 6,685,942 B1 | 2/2004 | Burton et al. | |
| 6,818,216 B2 | 11/2004 | Young et al. | |
| 7,029,872 B2 | 4/2006 | Gerngross | |
| 7,125,689 B2 | 10/2006 | Carr et al. | |
| 7,364,737 B2 | 4/2008 | Burton et al. | |
| 7,449,308 B2 | 11/2008 | Gerngross et al. | |
| 7,488,477 B2 | 2/2009 | Pilkington et al. | |
| 7,867,497 B2 | 1/2011 | Crowe, Jr. | |
| 8,221,759 B2 | 7/2012 | Pilkington et al. | |
| 8,568,726 B2 | 10/2013 | Beaumont et al. | |
| 2002/0141990 A1 | 10/2002 | Deen et al. | |
| 2004/0005324 A1 | 1/2004 | Pilkington et al. | |
| 2004/0234528 A1 | 11/2004 | Burton et al. | |

(Continued)

FOREIGN PATENT DOCUMENTS

EP 548190 6/1993
EP 636182 2/1995

(Continued)

OTHER PUBLICATIONS

Chargelegue et al., A Peptide Mimic of a Protective Epitope of Respiratory Syncytial Virus Selected from a Combinitorial Library Induces Virus-neutralizing antibodies and reduces viral load in vivo, J. Virol., 1998, Issue 3, pp. 2040-2046, vol. 72.
Corti et al., Cross-neutralization of four paramyxoviruses by a human monoclonal antibody, Letter, 2013, pp. 439-443, vol. 19.
Johnston, et al., The Immunoreceptor TIGIT Regulates Antitumor and Antibiral CD8+ T Cell Effector Function, Cancer Cell, 2014, pp. 923-937, vol. 26.
Levin et al., Vstm3 is a member of the CD28 family end an important modulator for T-cell function, Eur. J. Immunol, 2011, pp. 902-915, vol. 41.
Lozano et al, The TIGIT CD226 Axis Regulates Human T Cell Function, The Journal of Immunology, 2012, pp. 3869-3875, vol. 188.
Null et al., Safety and Immunigenicity of Palivizumab (Synagis) administered for two seasons, Pediatr. Infect. Dis. J., 2005, Issue 11, pp. 1021-1023, vol. 24.
Stanietsky et al., The Interaction of TIGIT with PVR and PVRL2 Inhibits Human NK Cell Gytotoxicity, PNAS, 2009, pp. 17856-17863, vol. 106.

(Continued)

*Primary Examiner* — Barry A Chestnut
(74) *Attorney, Agent, or Firm* — Matthew A. Leff; Laura M. Ginkel

(57) ABSTRACT

The present invention relates to monoclonal antibodies which have high anti-RSV neutralizing titers. The invention further provides for isolated nucleic acids encoding the antibodies of the invention and host cells transformed therewith. The invention yet further provides for diagnostic, prophylactic and therapeutic methods employing the antibodies and nucleic acids of the invention, particularly as a passive immunotherapy agent in infants and the elderly.

13 Claims, 7 Drawing Sheets

Specification includes a Sequence Listing.

(56) References Cited

U.S. PATENT DOCUMENTS

| | | | |
|---|---|---|---|
| 2005/0019758 | A1 | 1/2005 | Deen et al. |
| 2005/0175986 | A1 | 8/2005 | Gross et al. |
| 2006/0057702 | A1 | 3/2006 | Rosenthal et al. |
| 2006/0159695 | A1 | 7/2006 | Delvecchio et al. |
| 2009/0092609 | A1 | 4/2009 | Crowe, Jr. |
| 2009/0110684 | A1 | 4/2009 | Pilkington et al. |
| 2010/0021470 | A1 | 1/2010 | Lanzavecchia |
| 2011/0027294 | A1 | 2/2011 | Delvecchio et al. |
| 2011/0158985 | A1 | 6/2011 | Losonsky et al. |
| 2012/0027768 | A1 | 2/2012 | Lanzavecchia |
| 2012/0087909 | A1 | 4/2012 | Pilkington et al. |
| 2014/0004123 | A1 | 1/2014 | Lanzavecchia |
| 2014/0271653 | A1 | 9/2014 | Gurnett-Bander et al. |

FOREIGN PATENT DOCUMENTS

| | | |
|---|---|---|
| EP | 851924 | 7/1998 |
| EP | 977590 | 2/2000 |
| EP | 853487 | 7/2000 |
| EP | 1229125 | 8/2002 |
| EP | 671927 | 1/2003 |
| EP | 1178829 A4 | 6/2005 |
| EP | 854730 | 5/2009 |
| EP | 2201040 A1 | 6/2010 |
| EP | 1885402 A4 | 11/2010 |
| WO | WO9204381 | 3/1992 |
| WO | WO9406448 | 3/1994 |
| WO | WO9429351 | 12/1994 |
| WO | WO9711177 | 3/1997 |
| WO | WO0042072 | 7/2000 |
| WO | WO03011878 | 2/2003 |
| WO | WO03086310 | 10/2003 |
| WO | WO2005120571 | 12/2005 |
| WO | WO2006014679 | 2/2006 |
| WO | WO2006050280 | 5/2006 |
| WO | WO2008147196 | 12/2008 |
| WO | WO2006110214 A3 | 4/2009 |
| WO | WO2009042589 A1 | 4/2009 |
| WO | WO2009126688 | 10/2009 |
| WO | WO2014089169 | 6/2014 |
| WO | WO2014121021 | 8/2014 |

OTHER PUBLICATIONS

Wu et al., Characterization of the epitope for anti-human respiratory syncytial virus F protein monoclonal antibody 101F using synthetic peptides and genetic approaches, J. Gen. Virol, 2007, pp. 2719-2723, vol. 88.
Young et al., Developmentof a potent respiratory syncytial virus specific monoclonal antibody for the prevention of serious lower respiratory tract disease in Infants, Respir. Med., 2002, pp. 31-35, vol. 96.
S. Angal et al., A Single Amino Acid Substitution Abolishes the Heterogeneity of Chimeric Mouse/Human (IgG4) Antibody, Molecular Immunology, 1993, 105-108, 30(1).
Judy A. Beeler et al., Neutralization Epitopes of the F glycoprotein of Respiratory Syncytial Virus: Effect of Mutation upon Fusion Function, Journal of Virology, 1989, 2941-2950, 63(7).
Rainer Bischoff et al., Deamidation of asparagine and gutamine residues in proteins and peptides: structural determinants and analytical methodology, Journal of Chromatography B., 1994, 261-278, 662.
McKay Brown et al., Tolerance of single, but not multiple, amino acid replacements in antibody VH CDR 2: a means of minimizing B cell wastage from somatic hypermutation?, The Journal of Immunology, 1996, 3285-3291, 156 (9).
Byung-Kwon Choi et al., Use of combinatorial genetic libraries to humanize N-linked glycosylation in the yeast Pichia pastoris, Proc Natl Acad Sci USA, 2003, 5022-5027, 100(9).

William F. Dall'Acqua et al., Properties of Human IgG1s Engineered for Enhanced Binding to the Neonatal Fc Receptor (FcRn), Journal of Biological Chemistry, 2006, 23514-23524, 281(33).
Blanca Garcia-Barreno et al., Marked Differences in the Antigenic Structure of Human Respiratory Syncytial Virus F and G glycoproteins, Journal of Virology, 1989, 925-932, 63(2).
Barney S. Graham et al., Novel antigens for RSV vaccines, Current Opinion in Immunology, 2015, 30-38, 35.
Stephen R. Hamilton et al., Production of Complex Human Glycoproteins in Yeast, Science, 2003, 1244-1246, 301.
Stephen R. Hamilton et al., Humanization of Yeast to Produce Complex Terminally Sialylated Glycoproteins, Science, 2006, 1441-1443, 313.
Stephen R. Hamilton et al., Glycosylation engineering in yeast: the advent of fully humanized yeast, Current Opinion in Biotechnology, 2007, 387-392, 18.
E. J. Israel et al., Increased clearance of IgG in mice that lackB2-microglobulin: possible protective role of FcRn, Immunology, 1996, 573-578, 89.
Greg A. Lazar et al., Engineered antibody Fc variants with enhanced effector function, Proc Natl Acad Sci USA, 2006, 4005-4010, 103(11).
Huijuan Li et al., Optimization of humanized IgGs in glycoengineered Pichia pastoris, Nature Biotechnology, 2006, 210-215, 24(2).
Jason S. McLellan et al., Structure of Respiratoly Syncytial Virus Fusion Glycoprotein in the Postfusion Confirmation Reveals Preservation of Neutralizing Epitopes, Journal of Virology, 2011, 7788-7796, 85(15).
Jason S. McLellan et al., Structure-Based Design of a Fusion Glycoprotein Vaccine for Respiratory Syncytial Virus, Science, 2013, 592-598, 342(6158).
Jason S. McLellan et al., Structure of RSV Fusion glycoprotein Trimer Bound to a Profusion-Specific Neutralizing Antibody, Science, 2013, 1113-1117, 340(6136).
Nechansky et al., Compensationof endogenous IgG mediated inhibition of antibody-dependent cellular cytotoxicity by glycoengineering of therapeutic antibodies, Molecular Immunology, 2007, 1815-1817, 44.
Juergen H. Nett et al., A combinatorial genetic library approach to target heterologous glycosylation enzymes to the endoplasmic reticulum or the Golgi apparatus of Pichia pastoris, Yeast, 2011, 237-252, 28.
Vaheh Oganesyan et al., Structural characterization of a human Fc fragment engineered for extended serum half-life, Mol Immunology, 2009, 1750-1755, 46.
Leonard G. Presta et al., Selection, design, and engineering of therapeutic antibodies, J. Allergy Clin. Immunol., 2005, 731-736, 116(4).
K.J. Reissner et al., Deamidation and isoaspartate formation in proteins: unwanted alterations or surreptitious signals?, Cell. Mol. Life Sci., 2003, 1281-1295, 60.
Gabriel J. Robbie et al., A Novel Investigational Fc-Modified Humanized Monoclonal Antibody, Motavizumba-YTE, Has an Extended Half-Life in Healthy Adults, Antimicrobial Agents and Chemotherapy, 2013, 6147-6153, 57(12).
Robert L. Shields et al., High Resolution Mapping of the Bidning Site on Human IgG1 for FcyRI, FcyRII, FcyRIII, and ReRn and Design of IgG1 Variants with Improved Binding to the FcyR*, The Journal of Biological Chemistry, 2001, 6591-6604, 276(9).
G. Taylor et al., Monoclonal antibodies protect against respiratory syncytial virus infection in mice, Immunology, 1984, 137-142, 52.
Edward E. Walsh et al., Protection from Respiratory Syncytial Virus Infection in Cotton Rats by Passive Transfer of Monoclonal Antibodies, Infection and Immunity, 1984, 756-758, 43(2).
Brett D. Welch et al., Structure of the cleavage-activated prefusion form of the parainfluenza virus 5 fusion protein, Proc Natl Acad Sci, 2012, 16672-16677, 109(41).
Genbank Accession AAR14266, F [Human Respiratory syncytial virus 9320], 2004.
U.S. Appl. No. 15/335,560, filed Oct. 27, 2016.

ANTIBODY NEUTRALIZING HUMAN RESPIRATORY SYNCYTIAL VIRUS

CROSS REFERENCE TO RELATED APPLICATIONS

The present application is a divisional application of U.S. Ser. No. 15/335,560 filed Oct. 27, 2016, and which claims benefit of U.S. Provisional Patent Application No. 62/247,841 filed Oct. 29, 2015, and U.S. Provisional Patent Application No. 62/367,359 filed Jul. 27, 2016, each of which are incorporated herein by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "24158_US_NP_SEQLIST_20OCTOBER2017", creation date of Dec. 20, 2017, and a size of 25 KB. This sequence listing submitted via EFS-Web is part of the specification and is herein incorporated by reference in its entirety.

FIELD OF THE INVENTION

The present invention relates to human monoclonal antibodies which have high anti-RSV neutralizing titers, as well as the use of these antibodies as a passive immunotherapy agent in infants and the elderly.

BACKGROUND OF THE INVENTION

Paramyxoviruses are enveloped negative-strand RNA viruses that are significant human and animal pathogens. Human Respiratory Syncytial Virus (hRSV, RSV) belongs to the family Paramyxoviridae, subfamily Pneumovirinae. Two subtypes, type A and type B, have been identified and are a major cause of severe and sometimes even fatal respiratory infections in children less than 6 months of age. Adults with underlying diseases, such as COPD, asthma, cancer, immunocompromised status, including HIV or post transplantation, are also at risk of developing severe RSV infection. 15% of annual hospitalizations in adults over 50 years due to acute respiratory infection are caused by RSV. In the United States, RSV causes more than 100,000 hospitalizations annually, and it is estimated to cause about 160,000 deaths globally each year. Currently there is no vaccine for RSV, and a trial with a formalin-inactivated virus was associated with increased disease severity in infants upon infection with RSV. Other family members including Human Metapneumo Virus (hMPV) and Human Parainfluenza Virus (hPIV) are also responsible for acute respiratory illness similar to hRSV.

The hRSV genome is a single-stranded negative-sense RNA molecule of approximately 15 kb that encodes 11 proteins. Two of these proteins are the main surface glycoproteins of the virion. These are (i) the attachment (G) protein, which mediates virus binding to cells, and (ii) the fusion (F) protein, which promotes both fusion of the viral and cell membranes at the initial stages of the infectious cycle and fusion of the membrane of infected cells with those of adjacent cells to form characteristic syncytia. The attachment protein G binds cellular surface receptors and interacts with F. This interaction triggers a conformational change in F to induce membrane fusion, thereby releasing the viral ribonucleoprotein complex into the host cell cytoplasm.

Monoclonal antibodies against the F protein or the G protein have been shown to have neutralizing effect in vitro and prophylactic effects in vivo. See, e.g., Beeler and Coelingh 1989, J. Virol. 63:2941-50; Garcia-Barreno et al., 1989, J. Virol. 63:925-32; Taylor et al., 1984, Immunology 52: 137-142; Walsh et al., 1984, Infection and Immunity 43:756-758; and U.S. Pat. Nos. 5,842,307 and 6,818,216. Neutralizing epitopes on the F glycoprotein were originally mapped by identifying amino acids that were altered in antibody escape variants and by assessing antibody binding to RSV F-derived peptides. These studies demonstrated neutralizing antibodies are often targeted to two distinct linear epitopes. See Graham et al., 2015, Curr Opin Immunol 35:30-38 for a review of the antigenic sites for the pre-fusion and post-fusion F forms. Antigenic site II (also called site A) includes residues 255 to 275 and is the target of palivizumab (SYNAGIS®, AstraZeneca). This epitope was predicted to be conformationally dependent, and the structure of a more potent derivative of palivizumab in complex with this epitope revealed that the linear epitope adopts a helix-loop-helix conformation. Antigenic site IV (also called site C) includes residues 422 to 438 and is the target of antibodies MAb19 and 101F. This epitope is C-terminal to the cysteine-rich region and is part of domain II, which in homologous paramyxovirus F glycoproteins remains structurally unchanged between pre- and post-fusion conformations. 5C4, AM22 and D25 delineate an epitope designated as site 0 which is only present on the pre-fusion F protein and were 50 times as potent as palivizumab. See McLellan et al., 2013, Science 340:1113-1117; International Patent Application No. WO 2008/147196 and U.S. Pat. No. 8,568,726. Other hRSV antibodies are described in International Patent Application Nos. WO94/06448 and WO92/04381 and U.S. Pat. No. 8,221,759.

An RSV vaccine for active immunization, if available, could not be utilized for the treatment of newborn babies with immature immune systems or patients who are immunosuppressed. In patients where prophylactic passive immunotherapy is required, as a result of a more chronic form of disease, current therapy is mediated via periodic intravenous inoculation of human IgG prepared from pooled plasma. This type of therapy, due to the low titers of neutralizing anti-RSV antibodies, involves a large quantity of globulin (e.g., 0.75 gm per kg) and consequently requires administration intravenously, in a clinic or hospital, over a lengthy period (2 to 4 hours), on a monthly basis during the high risk months (fall, winter and early spring).

SUMMARY OF THE INVENTION

The invention provides anti-RSV F-protein antibodies and antigen binding fragments thereof comprising the structural and functional features specified below.

In one embodiment, the invention provides an antibody or antigen binding fragment thereof that binds to human RSV F-protein, comprising: a heavy chain variable region CDR3 comprising the amino acid sequence of SEQ ID NO: 3. In certain embodiments, the heavy chain or heavy chain variable region does not comprise the amino acid sequence of SEQ ID NO: 9. In one embodiment, the antibody or antigen binding fragment thereof optionally has at least one of the following characteristics: (i) binds to human RSV pre-fusion F protein with a Kd value of about $1\times10^{-9}$ M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-6}$ M to about $1\times10^{-9}$ M as determined by surface plasmon resonance (e.g., BIACORE) or a similar technique (e.g. KinExa or OCTET). In certain embodiments, the heavy chain comprises, consists essentially of, or consists of, the amino acid sequence of SEQ ID NO: 23.

In another embodiment, the invention provides an antibody or antigen binding fragment thereof that binds to human RSV F-protein, comprising: a light chain variable region CDR3 comprising the amino acid sequence of SEQ ID NO: 6. In certain embodiments, the light chain or light chain variable region does not comprise the amino acid sequence of SEQ ID NO: 8. In certain embodiments, the light chain is not associated with a heavy chain comprising the amino acid sequence of SEQ ID NO: 9. In certain embodiments, the light chain is associated with a heavy chain comprising the amino acid sequence of SEQ ID NO: 7. In one embodiment, the antibody or antigen binding fragment thereof optionally has at least one of the following characteristics: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the light chain comprises, consists essentially of, or consists of, the amino acid sequence of SEQ ID NO: 25.

In another embodiment, the invention provides an antibody or antigen binding fragment thereof that binds to human RSV F-protein comprising: (i) a heavy chain variable region CDR1 comprising the amino acid sequence of SEQ ID NO: 1; (ii) a heavy chain variable region CDR2 comprising the amino acid sequence of SEQ ID NO: 2; and (iii) a heavy chain variable region CDR3 comprising the amino acid sequence of SEQ ID NO: 3. In certain embodiments, the heavy chain or heavy chain variable region does not comprise the amino acid sequence of SEQ ID NO: 9. In one embodiment, the antibody or antigen binding fragment thereof optionally has at least one of the following characteristics: (i) binds to human RSV pre-fusion F protein with a Kd value of about $1\times10^{-9}$M to about $1\times10^{-12}$M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the heavy chain comprises, consists essentially of, or consists of, the amino acid sequence of SEQ ID NO: 23.

In one embodiment, the antibody or antigen binding fragment thereof comprises: (i) a light chain variable region CDR1 comprising the amino acid sequence of SEQ ID NO: 4; (ii) a light chain variable region CDR2 comprising the amino acid sequence of SEQ ID NO: 5; and (iii) a light chain variable region CDR3 comprising the amino acid sequence of SEQ ID NO: 6. In certain embodiments, the light chain or light chain variable region does not comprise the amino acid sequence of SEQ ID NO: 8. In certain embodiments, the light chain is not associated with a heavy chain comprising the amino acid sequence of SEQ ID NO: 9. In certain embodiments, the light chain is associated with a heavy chain comprising the amino acid sequence of SEQ ID NO: 7. In one embodiment, the antibody or antibody fragment thereof optionally has at least one of the following characteristics: (i) binds to human RSV pre-fusion F protein with a Kd value of about $1\times10^{-9}$ M to about $1\times10^{-12}$M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$ M as determined by surface plasmon resonance (e.g., BIACORE) or a similar technique (e.g. KinExa or OCTET) In certain embodiments, the light chain comprises, consists essentially of, or consists of, the amino acid sequence of SEQ ID NO: 25.

In one embodiment, the antibody or antigen binding fragment thereof comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In one embodiment, the antibody or antigen binding fragment thereof optionally has at least one of the following characteristics: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In another embodiment, the invention provides an antibody or antigen binding fragment that binds to human RSV F-protein comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6; wherein the antibody or antigen binding fragment thereof comprises a heavy chain variable region comprising at least 90%, 95%, 96%, 97%, 98% or 99% identity to a heavy chain variable region consisting of SEQ ID NO: 7 and a light chain variable region comprising at least 90%, 95%, 96%, 97%, 98% or 99% identity to a light chain variable region consisting of SEQ ID NO: 8. In certain embodiments, the heavy chain or heavy chain variable region does not comprise the amino acid sequence of SEQ ID NO: 9. In these aforementioned embodiments, the sequence variations occur in the framework regions. In one embodiment, the antibody or antigen binding fragment thereof optionally has at least one of the following characteristics: (i) binds to human RSV pre-fusion F protein with a Kd value of about $1\times10^{-9}$M to about $1\times10^{-12}$ M as determined by surface plasmon resonance (e.g., BIACORE)

or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In another embodiment, the invention also provides an antibody or antigen binding fragment thereof that binds to human RSV comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In one embodiment, the antibody or antigen binding fragment thereof comprises 1, 2 or 3 amino acid substitutions in the heavy chain CDRs (SEQ ID NOs: 1-3) and/or in the light chain CDRs (SEQ ID NOs: 4-6). The VH sequence of SEQ ID NO: 7 has the CDRs of SEQ ID NOs:1-3; and the VL sequence of SEQ ID NO: 8 has the CDRs of SEQ ID NOs: 4-6. In one embodiment, the antibody or antigen binding fragment thereof optionally has at least one of the following characteristics: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In one embodiment, the invention provides an antibody or antigen binding fragment thereof, comprising: a variable heavy chain comprising the amino acid sequence of SEQ ID NO: 7 and/or a variable light chain comprising the amino acid sequence of SEQ ID NO: 8, wherein the antibody or antigen binding fragment thereof binds to human RSV F protein. In another embodiment, the antibody or antigen binding fragment thereof comprises a heavy chain comprising, consisting essentially of, or consisting of, the amino acid sequence of SEQ ID NO: 23 and a light chain comprising, consisting essentially of, or consisting of, the amino acid sequence of SEQ ID NO: 25, wherein the antibody or antigen binding fragment thereof binds to human RSV F protein. In one embodiment, the antibody or antigen binding fragment thereof optionally has at least one of the following characteristics: (i) binds to human RSV pre-fusion F protein with a Kd value of about $1\times10^{-9}$ M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$ M as determined by surface plasmon resonance (e.g., BIACORE) or a similar technique (e.g. KinExa or OCTET).

In another embodiment, the invention provides an antibody or antigen binding fragment thereof that binds to the same epitope of human RSV F protein as an antibody comprising the heavy chain of SEQ ID NO: 23 and the light chain of SEQ ID NO: 25, wherein the antibody or antigen binding fragment thereof has at least one of the following characteristics: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$ M as determined by surface plasmon resonance (e.g., BIACORE) or a similar technique (e.g. KinExa or OCTET). In one embodiment, the antibody comprises at least 80%, 85%, 90%, 95%, 96%, 97%, 98% or 99% sequence identity with the heavy chain variable region and/or the light chain variable region of SEQ ID NOs: 7 and 8, respectively. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the heavy chain variable region of SEQ ID NO: 7 and/or the light chain variable region of SEQ ID NO: 8. In certain embodiments, the heavy chain or heavy chain variable region does not comprise the amino acid sequence of SEQ ID NO: 9.

In another embodiment, the invention provides an antibody or antigen binding fragment thereof that cross-blocks the binding of (or competes with) an antibody comprising the heavy chain of SEQ ID NO: 23 and the light chain of SEQ ID NO: 25 to human RSV, wherein the antibody or antigen binding fragment thereof has at least one of the following characteristics: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In one embodiment, the antibody or antigen binding fragment thereof comprises at least 80%, 85%, 90%, 95%, 96%, 97%, 98% or 99% sequence identity with the heavy chain variable region of SEQ ID NO: 7 or the light chain variable region of SEQ ID NO: 8. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the heavy chain variable region of SEQ ID NO: 7 or the light chain variable region of SEQ ID NO: 8. In another embodiment, the antibody or antigen binding fragment thereof comprises 1, 2 or 3 amino acid substitutions in the heavy chain CDRs (SEQ ID NOs: 1-3) and/or in the light chain CDRs (SEQ ID NOs: 4-6). In certain embodiments, the heavy chain or heavy chain variable region does not comprise the amino acid sequence of SEQ ID NO: 9.

In one embodiment, the invention relates to an isolated antibody or antigen binding fragment that binds to human RSV F protein comprising: a heavy chain comprising the amino acid sequence of SEQ ID NO: 7 or variant thereof comprising up to 30 amino acid substitutions, and/or a light chain comprising the amino acid sequence of SEQ ID NO: 8 comprising up to 12 amino acid substitutions. In certain embodiments, the heavy chain or heavy chain variable region does not comprise the amino acid sequence of SEQ ID NO: 9.

In certain embodiments, the invention relates to an isolated antibody or antigen binding fragment that binds to human RSV F protein, wherein the antibody binds to human RSV F protein through one or more of the following interactions or all of the following interactions:

1) the light chain CDR3 loop, through residues Phe 91 and Leu 92, interacts with the side chain of Arg 429 of human RSV F protein through the formation of two hydrogen bonds between the carbonyl oxygens of Phe 91 and Leu 92 in the CDR3 loop and the guanidino nitrogens of Arg 429 of human RSV F protein;
2) the light chain CDR2 loop, through residues Asp 50 and Glu 55, forms hydrogen bonds with Asn 426 and Lys 445 of human RSV F protein;
3) the heavy chain CDR3 loop, through residues Tyr 104 and Tyr 110, form a surface for van der Waals interaction with Ile 432 on human RSV F protein;
4) the heavy chain CDR3 loop, through Asn 107, forms a hydrogen bond with Lys 433 of human RSV F protein; and
5) the light chain packs against Glu 161 and Ser 182 of the neighboring monomer of a RSV pre-fusion trimer.

In certain aspects of any of the above embodiments, the antibody or antigen binding fragment thereof is isolated.

In certain aspects of any of the above embodiments, the antibody or antigen binding fragment thereof is a recombinant antibody.

In certain aspects of any of the above embodiments, the antibody or antigen binding fragment thereof is a full-length antibody.

In certain aspects of any of the above mentioned embodiments, the antibody or antigen binding fragment thereof of the invention can comprise a heavy region variable region consisting of: (a) any of the variable heavy chains described above and (b) a leader peptide (for example, the leader peptide of SEQ ID NO: 10). In certain aspects of any of the above mentioned embodiments, the antibody or antigen binding fragment thereof of the invention can comprise a light chain variable region consisting of: (a) any of the variable light chains described above and (b) a leader peptide (for example, the leader peptide of SEQ ID NO: 10).

In certain aspects of any of the above mentioned embodiments, the antibody or antigen binding fragment thereof of the invention is an antibody comprising any of the variable heavy chains described above and any human heavy chain constant domain. In one embodiment, the antibody or antigen binding fragment thereof of the invention is of the IgG isotype, and comprises a human IgG1, IgG2, IgG3 or IgG4 human heavy chain constant domain. In one embodiment, the antibody or antigen binding fragment thereof of the invention comprises a human heavy chain IgG1 constant domain wherein the IgG1 constant domain is afucosylated.

In certain aspects of any of the above mentioned embodiments, the antibody or antigen binding fragment thereof of the invention can comprise any of the variable light chains described above and a human light chain constant domain. In one embodiment, the antibody or antigen binding fragment thereof of the invention comprises a human kappa light chain constant domain or a variant thereof, wherein the variant comprises up to 20, 10, 5, 3, 2, or 1 modified amino acid substitutions. In another embodiment, the antibody or antigen binding fragment thereof of the invention comprises a human lambda light chain constant domain or a variant thereof, wherein the variant comprises up to 20, 10, 5, 3, 2, or 1 modified amino acid substitutions. In one embodiment, the antibody or antigen binding fragment thereof of the invention comprises a human kappa light chain constant domain comprising the amino acid sequence of SEQ ID NO: 14.

In one embodiment, the anti-hRSV F-protein antibody of the invention comprises a full tetrameric structure having two light chains and two heavy chains, wherein each light chain comprises: a variable region comprising SEQ ID NO: 8 and a human kappa light chain constant domain (SEQ ID NO: 14); and each heavy chain comprises: a variable region comprising SEQ ID NO: 7 and a human IgG1 constant domain (SEQ ID NO: 13).

In certain aspects of any of the above mentioned embodiments, the anti-hRSV F-protein antibody or antigen binding fragment thereof of the invention can be conjugated to at least one prophylactic or therapeutic agent. In one embodiment, the therapeutic agent comprises a second antibody or fragment thereof, an immunomodulator, a hormone, a cytotoxic agent, an enzyme, a radionuclide, a second antibody conjugated to at least one immunomodulator, enzyme, radioactive label, hormone, antisense oligonucleotide, or cytotoxic agent, or a combination thereof.

The invention also provides isolated polypeptides comprising the amino acid sequence of any one of SEQ ID NOs: 1-8, 23 or 25, or a fragment of any said sequences. In certain embodiments, the polypeptides comprising heavy chain amino acid sequences do not comprise the amino acid sequence of SEQ ID NO: 9.

The invention also provides isolated nucleic acids encoding any one of the anti-hRSV F-protein antibodies or antigen binding fragments of the invention. In one embodiment, the invention provides isolated nucleic acids encoding any one of the polypeptides of SEQ ID NOs: 1-8, 23 or 25, wherein said polypeptides can optionally comprise a leader sequence. In certain embodiments, the polypeptides comprising heavy chain amino acid sequences do not comprise the amino acid sequence of SEQ ID NO: 9. The invention also provides expression vectors comprising a nucleic acid encoding any one of the polypeptides of SEQ ID NOs: 1-8, 23 or 25 (wherein said polypeptides can optionally comprise a leader sequence). In certain embodiments, the polypeptides comprising heavy chain amino acid sequences do not comprise the amino acid sequence of SEQ ID NO: 9. These isolated nucleic acids and the expression vectors comprising them may be used to express the antibodies of the invention or antigen binding fragments thereof in recombinant host cells. Thus, the invention also provides host cells comprising isolated nucleic acids encoding any one of the polypeptides of SEQ ID NOs: 1-8, 23 or 25 (wherein said polypeptides can optionally comprise a leader sequence). In certain embodiments, the polypeptides comprising heavy chain amino acid sequences do not comprise the amino acid sequence of SEQ ID NO: 9. In one embodiment, the host cell is Chinese hamster ovary cell. In one embodiment, the host cell is a yeast cell, for example a *Pichia* cell or a *Pichia pastoris* host cell.

The invention also provides pharmaceutical compositions comprising an antibody or antigen binding fragment of the invention and a pharmaceutically acceptable carrier or diluent. In one embodiment, the pharmaceutically acceptable carrier or diluent is L-Histidine. In one aspect of this embodiment, the antibody or antigen binding fragment is formulated in 10 mM L-Histidine, 7% (w/v) Sucrose, and 0.02% (w/v) polysorbate-80, pH 6.0. The antibody or antigen binding fragment is typically present at about 100 mg/mL in such a formulation.

In one embodiment, the present invention provides compositions comprising an antibody or antigen binding fragment thereof of the invention and comprising a further prophylactic or therapeutic agent. In one embodiment, the further prophylactic or therapeutic agent is selected from the group consisting of: a second anti-hRSV antibody or an antigen binding fragment thereof. In one embodiment, the second anti-hRSV antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9.

The invention also provides a vessel or injection device comprising any one of the anti-hRSV F-protein antibodies or antigen binding fragments of the invention. In one embodiment, the anti-hRSV F-protein antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

The invention also provides a method of producing an anti-hRSV F-protein antibody or antigen binding fragment of the invention comprising: culturing a host cell comprising a polynucleotide encoding a heavy chain and/or light chain of an antibody of the invention (or an antigen binding fragment thereof) under conditions favorable to expression of the polynucleotide; and optionally, recovering the antibody or antigen binding fragment from the host cell and/or culture medium. In one embodiment, the polynucleotide encoding the heavy chain and the polynucleotide encoding the light chain are in a single vector. In another embodiment, the polynucleotide encoding the heavy chain and the polynucleotide encoding the light chain are in different vectors. In one embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO:4; (v) a light chain variable region CDR2 comprising the amino acid sequence of SEQ ID NO:5; and (vi) a light chain variable region CDR3 comprising the amino acid sequence of SEQ ID NO:6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

The invention also provides a method of preventing or treating hRSV infection in a subject in need thereof, comprising administering to the subject an effective amount of an anti-hRSV F-protein antibody or antigen binding fragment of the invention, optionally in association with a further prophylactic or therapeutic agent or a therapeutic procedure. In one embodiment, the subject being treated is a human subject. In one embodiment, the further prophylactic or therapeutic agent is selected from the group consisting of: a second anti-hRSV antibody or an antigen binding fragment thereof, a nucleic acid encoding the anti-RSV F antibody or antigen binding fragment, or an antibody conjugate. In one embodiment, the anti-hRSV F-protein antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

The invention also provides a method of preventing or treating hRSV infection in a subject in need thereof, comprising administering to the subject an effective amount of an anti-hRSV F-protein antibody or antigen binding fragment of the invention, optionally in combination with a further prophylactic or therapeutic agent or a therapeutic procedure. In one embodiment, the anti-hRSV F-protein antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

The invention also provides a vaccine, or immunogenic composition, comprising an antibody or antigen binding fragment of the invention. In one embodiment, the anti-hRSV F-protein antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In one embodiment, the vaccine, or immunogenic composition, further comprises an antigen selected from RSV F protein and RSV G protein and fragments thereof.

The invention also provides a method for detecting the presence of RSV in a sample (by detecting F protein or a fragment thereof) comprising contacting the sample with an antibody or antigen binding fragment thereof of the invention and detecting the presence of a complex between the antibody or fragment and the peptide; wherein detection of the complex indicates the presence of RSV F protein. In one embodiment, the antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In certain embodiments, the heavy chain or heavy chain variable region does not comprise the amino acid sequence of SEQ ID NO: 9. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

The invention also provides a method of increasing the anti-hRSV activity of an anti-hRSV F-protein antibody comprising: obtaining a parental anti-hRSV F-protein antibody and increasing the effector function of the parental anti-hRSV F-protein antibody; wherein the activity of the resulting anti-hRSV F-protein antibody is increased as compared to the parental anti-hRSV F-protein antibody. As used herein, a "parental anti-antibody" refers to antibody having a wild-type Fc region and/or wild type glycosylation (i.e., glycosylation pattern resulting from expression of the polypeptide in a non-engineered mammalian host cell). The effector function of a parental antibody can be increased by mutating its Fc region or by altering its glycosylation, for example by making the antibody afucosylated (as discussed in further detail below). In one embodiment, the effector function of a parental anti-hRSV F-protein antibody is increased by making mutations in the Fc region of the parental anti-hRSV F-protein antibody. In another embodiment, the effector function of a parental anti-hRSV F-protein antibody is increased by removing the fucose residues from the antibody, or expressing the antibody in a host cell that has been genetically engineered to remove the activity of the enzyme that adds fucose to glycoproteins.

DETAILED DESCRIPTION

Abbreviations

Figure 1A:
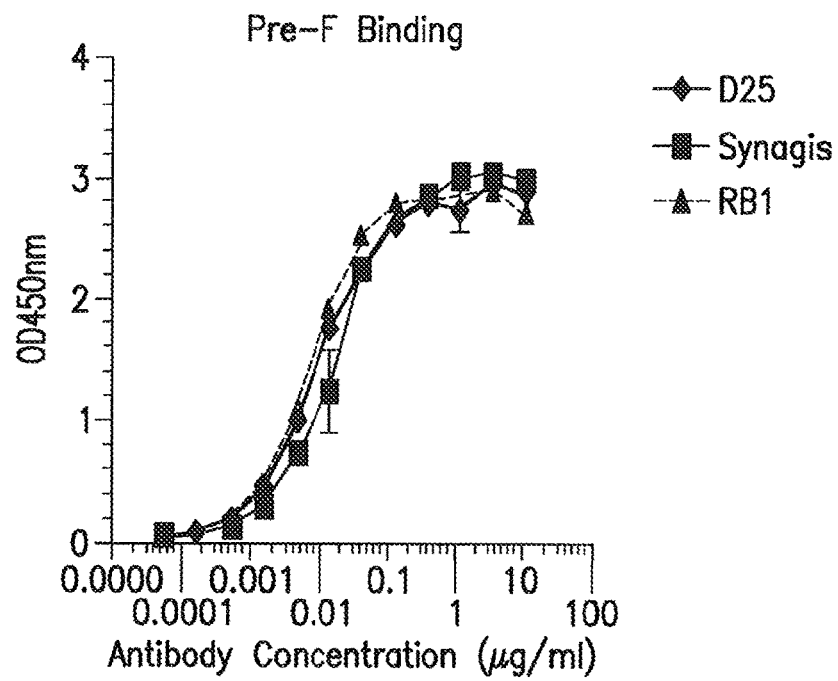
FIGS. 1A-B show binding curves (from ELISA) of human RSV antibodies D25, palivizumab, and RB1 to human RSV-F pre (A) and post (B) fusion proteins.

Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
ELISA Enzyme-linked immunosorbant assay
FR Antibody framework region: the immunoglobulin variable regions excluding the CDR regions
HRP Horseradish peroxidase
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"RSV disease" means any disease caused, directly or indirectly, by an infection with Respiratory Syncytial Virus (RSV) as well as diseases or conditions which predispose a patient to infection by RSV. Examples of diseases falling into the former category include pneumonia and bronchiolitis. Diseases and conditions in the latter category (i.e., those which place the patient at risk of severe RSV infection) include cystic fibrosis, congenital heart disease, cancer, age related immunosuppression, transplant recipients and, generally, any condition that causes a state of immunosuppression or decreased function of the immune system such as post-operative organ transplantation regimens or premature birth.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. Treatment with anti-RSV antibodies could also combined with other interventions (antibodies, nucleic acids, vaccines and small molecule compounds) to treat other respiratory pathogens.

"Prevent" or "preventing" means to administer a prophylactic agent, such as a composition containing any of the antibodies or antigen-binding fragments of the present invention, internally or externally to a subject or patient at risk of becoming infected by hRSV, for which the agent has prophylactic activity. Preventing includes reducing the likelihood or severity of a subsequent RSV infection, ameliorating symptoms associated with lower respiratory tract infection (LRI) upon RSV infection, and inducing immunity to protect against RSV infection. Typically, the agent is administered in an amount effective to neutralize RSV in the lungs and/or the nose in order block infection. The amount of a prophylactic agent that is effective to ameliorate any particular disease symptom may vary according to factors such as the age, and weight of the patient, and the ability of the agent to elicit a desired response in the subject. Whether a disease symptom has been ameliorated can be assessed by any clinical measurement typically used by physicians or other skilled healthcare providers to assess the severity or progression status of that symptom or in certain instances will ameliorate the need for hospitalization.

hRSV F Protein

Human RSV F protein is synthesized as a metastable trimeric precursor (F0) that is proteolytically cleaved into the covalently associated F1 and F2 subunits. Atomic structures of F trimers in the prefusion form have been determined for PIV5 and RSV members of paramyxoviridae family. See McLellan et al., 2011, J Virol. 85:7788-7796 (RSV) and Welch et al., 2012, Proc Natl Acad Sci 109: 16672-16677 (PIV). Prefusion F has a short C-terminal cytoplasmic tail, a single transmembrane domain, a helical stalk, and a globular head domain. Atomic structures of NDV, hPIV3, and RSV F in the postfusion form reveal that a large refolding event occurs to convert prefusion F to postfusion F in which part of the globular head domain rearranges to form a six helix bundle. These structures, along with peptide inhibitory data, suggest a model for F mediated membrane fusion where, upon activation, F1/F2 rearranges to insert a hydrophobic fusion peptide from the N-terminus of F1 into the target cell membrane forming a pre-hairpin intermediate. This relatively extended structure tethers the virus to the cell membrane and collapses to form the stable six-helix bundle of the postfusion structure. The transition from the metastable prefusion, to the prehairpin intermediate, to the postfusion conformation proceeds down an energy gradient with the postfusion form representing the most stable state, and the energy released during F refolding is coupled with membrane fusion.

The term hRSV F protein includes human RSV F protein as well as fragments thereof such as the mature fragment thereof lacking the signal peptide. In an embodiment of the invention, the amino acid sequence of human RSV F protein comprises the amino acid sequence disclosed in Genbank Accession Number AAR14266 (hRSV B strain 9320).

Anti-hRSV Antibodies and Antigen-Binding Fragments Thereof

The present invention provides antibodies or antigen-binding fragments thereof that bind human RSV F protein, preferably from both RSV A strains and B strains, that bind both the pre-fusion F protein and the post-fusion F protein, and uses of such antibodies or fragments. In some embodiments, the anti-RSV F-protein antibodies are isolated. The antibodies described herein bind to an epitope at site IV of the F protein. In any of the embodiments of the invention described herein, in certain embodiments, the heavy chain or heavy chain variable region does not comprise the amino acid sequence of SEQ ID NO: 9 and/or the light chain or light chain variable region does not comprise the amino acid sequence of SEQ ID NO: 8. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In preferred embodiments, the anti-RSV F-protein antibodies are fully human. A major advantage of the monoclonal antibodies of the invention derives from the fact that they include human CDR3 sequences and, in some embodiments, may be entirely human monoclonal antibodies. Hence in vivo use of the fully human monoclonal antibodies of the invention for immunoprophylaxis and immunotherapy of RSV disease greatly reduces the problem of host immune response to passively administered antibodies. This problem is commonly encountered when the prior art monoclonal antibodies of xenogeneic or chimeric derivation are utilized. A second important aspect of this advantage is the potential safety of these human monoclonal antibodies for gene therapy applications, in which expression of xenogeneic or chimeric proteins containing non-human sequences cannot be terminated.

As used herein, an anti-RSV F-protein antibody or antigen-binding fragment thereof refers to an antibody or antigen-binding fragment thereof that specifically binds to human RSV F protein. An antibody or antigen-binding fragment thereof that "specifically binds to human RSV" is an antibody or antigen-binding fragment thereof that binds to the pre-fusion or post-fusion human RSV F protein with a Kd of about 1 nM or a higher affinity (e.g., 1 nM-2 pM, 1 nM, 100 pM, 10 pM or 2 pM), but does not bind to other proteins lacking RSV F protein sequences. In one embodiment, the antibody of the invention which specifically binds to human RSV F protein is also cross-reactive with bovine RSV F protein. As used herein "cross-reactivity" refers to the ability of an antibody to react with a homologous protein from other species. Whether an antibody specifically binds to human RSV F protein can be determined using any assay known in the art. Examples of assays known in the art to determining binding affinity include surface plasmon resonance (e.g., BIACORE) or a similar technique (e.g. KinExa or OCTET).

The present invention includes anti-hRSV F-protein antibodies and methods of use thereof. As used herein, the term "antibody" refers to any form of antibody that exhibits the desired biological activity. Thus, it is used in the broadest sense and specifically covers, but is not limited to, monoclonal antibodies (including full length monoclonal antibodies comprising two light chains and two heavy chains), polyclonal antibodies, multispecific antibodies (e.g., bispecific antibodies), humanized antibodies, fully human antibodies, and chimeric antibodies.

The present invention includes anti-hRSV F-protein antigen-binding fragments and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g., fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., sc-Fv; and multispecific antibodies formed from antibody fragments.

The present invention includes anti-RSV F-protein Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-RSV F-protein antibodies and antigen-binding fragments thereof which comprise an Fc region and methods of use thereof. An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

The present invention includes anti-RSV F-protein Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

The present invention includes anti-RSV F-protein F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The present invention includes anti-RSV F-protein Fv fragments and methods of use thereof. The "Fv region" comprises the variable regions from both the heavy and light chains, but lacks the constant regions.

The present invention includes anti-RSV F-protein scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

The present invention includes anti-RSV F-protein domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-RSV F-protein bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-RSV F-protein diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, an antibody or antigen-binding fragment of the invention which is modified in some way retains at least 10% of its binding activity (when compared to the parental antibody) when that activity is expressed on a molar basis.

Preferably, an antibody or antigen-binding fragment of the invention retains at least 20%, 50%, 70%, 80%, 90%, 95% or 100% or more of the RSV F-protein binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-hRSV F-protein antibodies and antigen-binding fragments thereof and methods of use thereof. "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention includes monoclonal anti-hRSV F-protein antibodies and antigen-binding fragments thereof as well as monoclonal antibody compositions comprising a plurality of isolated monoclonal antibodies. The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods (see, e.g., U.S. Pat. No. 4,816, 567).

In general, the basic (or "full-length") antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region or domain of about 100 to 110 or more amino acids primarily responsible for antigen recognition. The carboxy-terminal portion of the heavy chain may define a constant region or domain primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989). In the context of an antibody or antigen binding fragment thereof, the terms domain and region can be used interchangeably, where appropriate.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat, 1978, *Adv. Prot. Chem.* 32:1-75; Kabat, et al., 1977, *J. Biol. Chem.* 252:6609-6616; Chothia et al., 1987, *J Mol. Biol.* 196:901-917 or Chothia et al., 1989, *Nature* 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk, 1987, J Mol. Biol. 196: 901-917 (defining the CDR regions of an antibody by structure). As used herein, the term "framework" or "FR" residues refers to those variable domain residues other than the hypervariable region residues defined herein as CDR residues.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell will be included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al., 2005, *Nucleic Acids Res*. 33:D256-D261.

Physical and Functional Properties of the Exemplary Anti-RSV F-Protein Antibodies The present invention provides anti-hRSV F-protein antibodies and antigen-binding fragments thereof having specified structural and functional features, and methods of use of the antibodies or antigen-binding fragments thereof in the treatment or prevention of diseases/conditions associated with RSV infection.

An "anti-RSV F-protein antibody or antigen-binding fragment thereof of the present invention" includes: any antibody or antigen-binding fragment thereof that is discussed herein (e.g., RB1) or a variant thereof (e.g., sequence variant or functional variant); any antibody or antigen-binding fragment comprising any one or more of the CDRs set forth in Table 7; any antibody or antigen-binding fragment that binds to the same epitope in human RSV F-protein as the antibodies discussed herein (e.g., RB1); and any antibody or antigen-binding fragment that cross-blocks (partially or fully) or is cross-blocked (partially or fully) by an antibody discussed herein (e.g., RB1) for RSV binding.

Cross-blocking antibodies and antigen-binding fragments thereof can be identified based on their ability to cross-compete with an antibody of the invention in standard binding assays (e.g., BIACore, ELISA, flow cytometry). For example, standard ELISA assays can be used in which a recombinant RSV F protein protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of another antibody (for example, antibody D25) to RSV F-protein demonstrates that the test antibody can compete with another antibody (e.g., D25) for binding to RSV F protein and thus, may, in some cases, bind to the same epitope on RSV F protein as antibody D25 to an overlapping epitope.

As stated above, antibodies and fragments thereof that bind to the same epitope as any of the anti-RSV F-protein antibodies or antigen-binding fragments thereof of the present invention also form part of the present invention. Further, in certain embodiments, antibodies that bind to an epitope that overlaps with the epitope bound by any of the anti-RSV F-protein antibodies of the invention also form part of the present invention. There are several methods available for mapping antibody epitopes on target antigens, including: H/D-Ex Mass spec, X-ray crystallography, pepscan analysis and site directed mutagenesis. For example, HDX (Hydrogen Deuterium Exchange) coupled with proteolysis and mass spectrometry can be used to determine the epitope of an antibody on a specific antigen Y. HDX-MS relies on the accurate measurement and comparison of the degree of deuterium incorporation by an antigen when incubated in $D_2O$ on its own and in presence of its antibody at various time intervals. Deuterium is exchanged with hydrogen on the amide backbone of the proteins in exposed areas whereas regions of the antigen bound to the antibody will be protected and will show less or no exchange after analysis by LC-MS/MS of proteolytic fragments.

Examples of the immunoglobulin chains of anti-RSV F-protein antibodies of the invention as well as their CDRs include, but are not limited those disclosed in Table 7 (SEQ ID NOs: 1-8, 23 and 25). The present invention includes any polypeptide comprising, consisting essentially of, or consisting of the amino acid sequences of SEQ ID NOs: 1-8, 23, and 25, and recombinant nucleotides encoding such polypeptides.

The scope of the present invention includes isolated anti-hRSV F-protein antibodies and antigen-binding fragments thereof, comprising a variant of an immunoglobulin chain set forth herein, e.g., any of SEQ ID NOs: 7, 8; wherein the variant exhibits one or more of the following properties: (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$M to about $1\times10^{-11}$M as determined by surface plasmon resonance (e.g., BIACORE) or a similar technique (e.g. KinExa or OCTET). In certain embodiments, the heavy chain or heavy chain variable region does not comprise the amino acid sequence of SEQ ID NO: 9.

In certain embodiments, the invention provides antibodies or antigen-binding fragment thereof that binds human hRSV F-protein and has $V_L$ domains and $V_H$ domains with at least 80%, 85%, 90%, 95%, 96%, 97%, 98% or 99% sequence identity with SEQ ID NOs: 8 ($V_L$) and 7 ($V_H$); wherein the variant exhibits the desired binding and properties, e.g., (i) binds to human RSV pre-fusion F protein with a Kd value of about $1\times10^{-9}$M to about $1\times10^{-12}$ M as determined by surface plasmon resonance (e.g., BIACORE) or a similar technique (e.g. KinExa or OCTET); or (ii) binds to human RSV post-fusion F protein with a Kd value of about $1\times10^{-9}$ M to about $1\times10^{-11}$M as determined by surface plasmon resonance (e.g., BIACORE) or a similar technique (e.g. KinExa or OCTET). In certain embodiments, the heavy chain or heavy chain variable region does not comprise the amino acid sequence of SEQ ID NO: 9.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 1. Also provided are isolated polypeptides comprising the $V_L$ domains of the anti-hRSV F-protein antibodies of the invention (e.g., SEQ ID NO: 8), and isolated polypeptides comprising the $V_H$ domains (e.g., SEQ ID NO: 7) of the anti-hRSV antibodies of the invention having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions, which may occur exclusively in the framework region or of which one or more may be located in one or more CDRs. In certain embodiments, the heavy chain or heavy chain variable region does not comprise the amino acid sequence of SEQ ID NO: 9.

In another embodiment, provided is an antibody or antigen-binding fragment thereof that binds hRSV F-protein and has $V_L$ domains and $V_H$ domains with at least 99% 98%, 97%, 96%, 95%, 90%, 85%, 80% or 75% sequence identity to one or more of the $V_L$ domains or $V_H$ domains described herein, and exhibits specific binding to hRSV F-protein. In another embodiment the binding antibody or antigen-binding fragment thereof of the present invention comprises $V_L$ and $V_H$ domains (with and without signal sequence) having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions, which may occur exclusively in the framework region or of which one or more may be located in one or more CDRs, and exhibits specific binding to hRSV F-protein. In certain embodiments, the heavy chain or heavy chain variable region does not comprise the amino acid sequence of SEQ ID NO: 9.

Polynucleotides and Polypeptides

The present invention further comprises the polynucleotides encoding any of the polypeptides or immunoglobulin chains of anti-hRSV F-protein antibodies and antigen-binding fragments thereof of the invention. In one embodiment, the isolated polynucleotide encodes an antibody or antigen-binding fragment thereof comprising at least one mature immunoglobulin light chain variable ($V_L$) domain according to the invention and/or at least one mature immunoglobulin heavy chain variable ($V_H$) domain according to the invention. In some embodiments the isolated polynucleotide encodes both a light chain and a heavy chain on a single polynucleotide molecule, and in other embodiments the light and heavy chains are encoded on separate polynucleotide molecules. In another embodiment the polynucleotides further encodes a signal sequence. For example, the present invention includes the polynucleotides encoding the amino acids described in SEQ ID NOs: 1-8, 23 and 25, as well as polynucleotides which hybridize thereto and, also, any polypeptide encoded by such a hybridizing polynucleotide. In one embodiment, the invention comprises a nucleic acid sequence comprising, consisting essentially of, or consisting of SEQ ID NO: 15 (variable heavy chain) or SEQ ID NO: 16 (variable light chain). In certain embodiments, codon optimization can be used to enhance a property of the nucleic acid, e.g., expression in a certain host. In one embodiment, the invention comprises a nucleic acid sequence comprising, consisting essentially of, or consisting of SEQ ID NO: 17 (codon optimized variable heavy) or SEQ ID NO: 18 (codon optimized variable light). In certain embodiments, a leader sequence can be used. In one embodiment, the invention comprises a nucleic acid sequence comprising, consisting essentially of, or consisting of SEQ ID NO: 19 (leader sequence and heavy chain) or SEQ ID NO: 20 (leader sequence and light chain) connected with the heavy chain or light chain to give SEQ ID NO: 21 or SEQ ID NO: 22, respectively.

In general, the polynucleotides hybridize under low, moderate or high stringency conditions, and encode antibodies or antigen-binding fragments thereof that maintain the ability to bind to hRSV F-protein. A first polynucleotide molecule is "hybridizable" to a second polynucleotide molecule when a single stranded form of the first polynucleotide molecule can anneal to the second polynucleotide molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65°

C. or 68° C.). In general, SSC is 0.15M NaCl and 0.015M Na-citrate. Hybridization requires that the two polynucleotides contain complementary sequences, although, depending on the stringency of the hybridization, mismatches between bases are possible. The appropriate stringency for hybridizing polynucleotides depends on the length of the polynucleotides and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra, 9.50-9.51). For hybridization with shorter polynucleotides, e.g., oligonucleotides, the position of mismatches becomes more important, and the length of the oligonucleotide determines its specificity (see Sambrook, et al., supra, 11.7-11.8).

In one embodiment, the invention comprises an isolated polynucleotide encoding an antibody heavy variable ($V_H$) domain or an antigen-binding fragment thereof comprising CDR-H1 (SEQ ID NO: 1), CDR-H2 (SEQ ID NO: 2) and CDR-H3 (SEQ ID NO: 3).

In one embodiment, the invention comprises an isolated polynucleotide encoding an antibody light chain variable ($V_L$) domain or an antigen-binding fragment thereof comprising CDR-L1 (SEQ ID NO: 4), CDR-L2 (SEQ ID NO: 5) and CDR-L3 (SEQ ID NO: 6).

In one embodiment, the invention comprises an isolated polynucleotide encoding the immunoglobulin heavy chain variable ($V_H$) domain of SEQ ID NO: 7 or a heavy chain of SEQ ID NO: 23.

In one embodiment, the invention comprises an isolated polynucleotide encoding the immunoglobulin heavy chain variable ($V_L$) domain of SEQ ID NO: 8 or a light chain of SEQ ID NO: 25.

This present invention also provides vectors, e.g., expression vectors, such as plasmids, comprising the isolated polynucleotides of the invention, wherein the polynucleotide is operably linked to control sequences that are recognized by a host cell when the host cell is transfected with the vector. Also provided are host cells comprising a vector of the present invention and methods for producing the antibody or antigen-binding fragment thereof or polypeptide disclosed herein comprising culturing a host cell harboring an expression vector or a nucleic acid encoding the immunoglobulin chains of the antibody or antigen-binding fragment thereof in culture medium, and isolating the antigen or antigen-binding fragment thereof from the host cell or culture medium.

Also included in the present invention are polypeptides, e.g., immunoglobulin polypeptides, comprising amino acid sequences that are at least about 75% identical, 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences (e.g. expect threshold: 10; word size: 3; max matches in a query range: 0; BLOSUM 62 matrix; gap costs: existence 11, extension 1; conditional compositional score matrix adjustment).

Sequence identity refers to the degree to which the amino acids of two polypeptides are the same at equivalent positions when the two sequences are optimally aligned.

The following references relate to BLAST algorithms often used for sequence analysis: BLAST ALGORITHMS: Altschul et al. (2005) *FEBS J.* 272(20): 5101-5109; Altschul, S. F., et al., (1990) *J. Mol. Biol.* 215:403-410; Gish, W., et al., (1993) *Nature Genet.* 3:266-272; Madden, T. L., et al., (1996) *Meth. Enzymol.* 266:131-141; Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock, J. M. et al., (1994) *Comput. Appl. Biosci.* 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, *Natl. Biomed. Res. Found.*, Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, *Natl. Biomed. Res. Found.*, Washington, D.C.; Altschul, S. F., (1991) *J. Mol. Biol.* 219:555-565; States, D. J., et al., (1991) *Methods* 3:66-70; Henikoff, S., et al., (1992) *Proc. Natl. Acad. Sci. USA* 89:10915-10919; Altschul, S. F., et al., (1993) *J. Mol. Evol.* 36:290-300; ALIGNMENT STATISTICS: Karlin, S., et al., (1990) *Proc. Natl. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Binding Affinity

By way of example, and not limitation, the antibodies and antigen-binding fragments disclosed herein may bind human RSV pre-fusion F protein or post-fusion F protein with a $K_D$ value of at least about $1\times10^{-9}$M (i.e, a $K_D$ value of $1\times10^{-9}$M or lower) as determined by surface plasmon resonance (e.g., BIACORE) or a similar technique (e.g. KinExa or OCTET). In one embodiment, the antibodies and antigen-binding fragments disclosed herein may bind human RSV pre-fusion F protein or post-fusion F protein with a $K_D$ value of at least about $1\times10^{-9}$M to about $1\times10^{-12}$M as determined by surface plasmon resonance (e.g., BIACORE) or a similar technique (e.g. KinExa or OCTET). In one embodiment, the antibodies and antigen-binding fragments disclosed herein may bind human RSV pre-fusion F protein or post-fusion F protein with a $K_D$ value of about $1\times10^{-9}$M to about $1\times10^{-12}$M as determined by surface plasmon resonance (e.g., BIACORE) or a similar technique (e.g. KinExa or OCTET). In one embodiment, the antibodies and antigen-binding fragments disclosed herein may bind human RSV pre-fusion F protein or post-fusion F protein with a $K_D$ value of at least about 100 pM (i.e, a $K_D$ value of about 100 pM or lower) as determined by BIACORE or a similar technique. In one embodiment, the antibodies and antigen-binding fragments disclosed herein may bind human RSV pre-fusion F protein or post-fusion F protein with a $K_D$ value of at least about 10 pM (i.e., a $K_D$ value of about 10 pm lower) as determined by BIACORE or a similar technique. In one embodiment, the antibodies and antigen-binding fragments of the invention may bind to human RSV pre-fusion F protein or post-fusion F protein with a $K_D$ of about 1 pM to about 100 pM as determined by BIACORE or a similar technique.

Methods of Making Antibodies and
Antigen-binding Fragments Thereof

The present invention includes methods for making an anti-hRSV F-protein antibody or antigen-binding fragment thereof of the present invention comprising culturing a cell line that expresses the antibody or fragment under conditions favorable to such expression and, optionally, isolating the antibody or fragment from the cells and/or the growth medium (e.g. cell culture medium).

The anti-hRSV F-protein antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., $V_H$ or $V_L$) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-hRSV antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-hRSV F-protein antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha,* any *Kluyveromyces* sp., *Candida albicans,* any *Aspergillus* sp., *Trichoderma reesei, Chrysosporium lucknowense,* any *Fusarium* sp., *Yarrowia lipolytica,* and *Neurospora crassa.* When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

Antibodies and antigen-binding fragments thereof and immunoglobulin chains can be recovered from the culture medium using standard protein purification methods. Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-hRSV antibody or antigen-binding fragment thereof of the present invention comprising introducing a sample comprising the antibody or fragment to a purification medium (e.g., cation exchange medium, anion exchange medium, hydrophobic exchange medium, affinity purification medium (e.g., protein-A, protein-G, protein-A/G, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

The present invention includes bispecific and bifunctional antibodies and antigen-binding fragments having a binding specificity for hRSV F protein and another antigen such as, for example, hRSV G protein, and methods of use thereof. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) *Clin. Exp. Immunol.* 79: 315-321, Kostelny, et al., (1992) *J Immunol.* 148:1547-1553. In addition, bispecific antibodies may be formed as "diabodies" (Holliger, et al., (1993) PNAS USA 90:6444-6448) or as "Janusins" (Traunecker, et al., (1991) *EMBO J* 10:3655-3659 and Traunecker, et al., (1992) *Int. J. Cancer Suppl.* 7:51-52).

The present invention further includes anti-hRSV F-protein antigen-binding fragments of the anti-hRSV antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG1, IgG2, IgG3 and IgG4; IgA1 and IgA2. The invention comprises antibodies and antigen-binding fragments of any of these classes or subclasses of antibodies.

In one embodiment, the antibody or antigen-binding fragment comprises a heavy chain constant region, e.g. a human constant region, such as γ1, γ2, γ3, or γ4 human heavy chain constant region or a variant thereof. In another embodiment, the antibody or antigen-binding fragment comprises a light chain constant region, e.g. a human light chain constant region, such as lambda or kappa human light chain region or variant thereof. By way of example, and not limitation the human heavy chain constant region can be γ4 and the human light chain constant region can be kappa. In an alternative embodiment, the Fc region of the antibody is γ4 with a Ser228Pro mutation (Schuurman, J et. al., 2001, *Mol. Immunol.* 38: 1-8).

In one embodiment, the antibody or antigen-binding fragment comprises a heavy chain constant region of the IgG1 subtype.

In some embodiments, different constant domains may be appended to $V_L$ and $V_H$ regions derived from the CDRs provided herein. For example, if a particular intended use of an antibody (or fragment) of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. The present invention includes anti-hRSV F-protein antibodies and antigen-binding fragments thereof which comprise an IgG4 constant domain, e.g., antagonist, humanized anti-hRSV F-protein antibodies and fragments, and methods of use thereof. In one embodiment, the IgG4 constant domain can differ from the native human IgG4 constant domain (Swiss-Prot Accession No. P01861.1) at a position corresponding to position 228 in the EU system and position 241 in the KABAT system, where the native Ser108 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) *Mol. Imunol.* 30:105. In other instances, a modified IgG1 constant domain which has been modified to increase half-life or reduce effector function can be used.

Antibody Engineering

The antibodies of the invention may be subject to framework mutations to improve the properties of the antibody. One such framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.*

662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for hRSV F-protein, or other desired biological activity to unacceptable levels.

TABLE 2

Exemplary stabilizing CDR variants

| CDR Residue | Stabilizing Variant Sequence |
|---|---|
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

Antibody Engineering of the Fc Region

The antibodies and antigen-binding fragments thereof disclosed herein (e.g., RB1) can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein (e.g., RB1) can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein (e.g., RB1) also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta, 2005, *J. Allergy Clin. Immunol.* 116:731 at 734-35.

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the antibody or antigen-binding fragment of the invention (e.g., RB 1) is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In one embodiment, a M252Y/S254T/T256E (YTE) mutation is introduced. See, e.g., Oganesyan et al., Mol. Immunol. 2009, 46:1750.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in International Patent Application Publication No. WO 94/29351.

In yet another example, the Fc region is modified to decrease the ability of the antibody or antigen-binding fragment of the invention (e.g., RB 1) to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in International Patent Application Publication No. WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604).

In one embodiment of the invention, the Fc region is modified to decrease the ability of the antibody of the invention (e.g., RB1) to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

Effector Function Enhancement

In some embodiments, the Fc region of an anti-hRSV antibody is modified to increase the ability of the antibody or antigen-binding fragment to mediate effector function and/or to increase their binding to the Fcgamma receptors (FcγRs).

The term "Effector Function" as used herein is meant to refer to one or more of Antibody Dependent Cell mediated Cytotoxic activity (ADCC), Complement-dependent cytotoxic activity (CDC) mediated responses, Fc-mediated phagocytosis or antibody dependent cellular phagocytosis (ADCP) and antibody recycling via the FcRn receptor.

The interaction between the constant region of an antigen binding protein and various Fc receptors (FcR) including FcgammaRI (CD64), FcgammaRII (CD32) and FcgammaRIII (CD16) is believed to mediate the effector functions, such as ADCC and CDC, of the antigen binding protein. The Fc receptor is also important for antibody cross-linking, which can be important for anti-tumor immunity.

Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al., 2001 *J. Biol. Chem., Vol.* 276, p 6591-6604; Chappel et al., 1993 *J. Biol. Chem.* 268: 25124-25131; Lazar et al., 2006, Proc Natl Acad Sci USA 103:4005-4010.

The ADCC or CDC properties of antibodies of the present invention, or their cross-linking properties, may be enhanced in a number of ways.

Human IgG1 constant regions containing specific mutations or altered glycosylation on residue Asn297 have been shown to enhance binding to Fc receptors. In some cases these mutations have also been shown to enhance ADCC and CDC (Lazar et al., Proc Natl Acad Sci USA 2006, 103:4005-4010; Shields et al., J Biol Chem 2001, 276:6591-6604; Nechansky et al., Mol Immunol 2007, 44:1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment, the antigen binding protein of the invention herein described is mutated at positions 239 and 332, for example S239D and I332E or in a further embodiment it is mutated at three or more positions selected from 239 and 332 and 330, for example S239D and I332E and A330L. (EU index numbering).

In an alternative embodiment of the present invention, there is provided an antibody comprising a heavy chain constant region with an altered glycosylation profile such that the antigen binding protein has enhanced effector function. For example, wherein the antibody has enhanced ADCC or enhanced CDC or wherein it has both enhanced ADCC and CDC effector function. Examples of suitable methodologies to produce antigen binding proteins with an altered glycosylation profile are described in International Patent Application Publication Nos. WO2003011878 and WO2006014679 and European Patent Application No. EP1229125.

In a further aspect, the present invention provides "non-fucosylated" or "afucosylated" antibodies. Non-fucosylated antibodies harbor a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcγRIIIa binding capacity.

The present invention also provides a method for the production of an antibody according to the invention comprising the steps of: a) culturing a recombinant host cell comprising an expression vector comprising an isolated nucleic acid as described herein, wherein the recombinant host cell does not comprise an alpha-1,6-fucosyltransferase; and b) recovering the antigen binding protein. The recombinant host cell may be not normally contain a gene encoding an alpha-1,6-fucosyltransferase (for example yeast host cells such as *Pichia* sp.) or may have been genetically modified to inactive an alpha-1,6-fucosyltransferase. Recombinant host cells which have been genetically modified to inactivate the FUT8 gene encoding an alpha-1,6-fucosyltransferase are available. See, e.g., the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. Nos. 7,214,775; 6,946,292; and International Patent Application Nos. WO0061739 and WO0231240. Those of ordinary skill in the art will also recognize other appropriate systems.

It will be apparent to those skilled in the art that such modifications may not only be used alone but may be used in combination with each other in order to further enhance effector function.

Production of Antibodies with Modified Glycosylation

In still another embodiment, the antibodies or antigen-binding fragments of the invention (e.g., RB1) comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a hRSV F-protein antigen. Such modifications can be accomplished by, for example, altering one or more of the glycosylation sites within the antibody or fragment sequence. For example, one or more amino acid substitutions can be made that result removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Antibodies and antigen-binding fragments disclosed herein (e.g., RB1) may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci. USA* 100: 5022-5027; Hamilton et al., (2003) *Science* 301: 1244-1246; Hamilton et al., (2006) *Science* 313: 1441-1443; Nett et al., (2011) *Yeast*

28(3):237-52; Hamilton et al., (2007) *Curr Opin Biotechnol. October;* 18(5):387-92). These genetically modified host cells have the ability to control the glycosylation profile of glycoproteins that are produced in the cells such that compositions of glycoproteins can be produced wherein a particular N-glycan structure predominates (see, e.g., U.S. Pat. No. 7,029,872 and U.S. Pat. No. 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein (e.g., RB 1) further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein (e.g., RB 1) may comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein (e.g., RB 1) comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans in comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc_{1-2})Man_3GlcNAc_2$, $NANAGal_2GlcNAc_2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects, the antibodies or antigen-binding fragments thereof comprise high mannose N-glycans, including, but not limited to, $Man_8GlcNAc_2$, $Man_7GlcNAc_2$, $Man_6GlcNAc_2$, $Man_5GlcNAc_2$, $Man_4GlcNAc_2$, or N-glycans that consist of the $Man_3GlcNAc_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G–2", "G–1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The antibodies and antigen-binding fragments thereof disclosed herein (e.g., RB1) may further contain one or more glycosylation sites in either the light or heavy chain immunoglobulin variable region. Certain glycosylation sites can result in decreased immunogenicity of the antibody or fragment or an alteration of the pK of the antibody due to altered antigen-binding (Marshall et al., 1972, *Annu Rev Biochem* 41:673-702; Gala and Morrison, 2004, *J Immunol* 172:5489-94; Wallick et al., 1988, *J Exp Med* 168:1099-109; Spiro, 2002, *Glycobiology* 12:43R-56R; Parekh et al., 1985, *Nature* 316:452-7; Mimura et al., 2000, *Mot Immunol* 37:697-706). Glycosylation has been known to occur at motifs containing an N-X-S/T sequence.

Each antibody or antigen-binding fragment (e.g., RB1) will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment (e.g., RB1) will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al., (2003) *Pharm Res* 20:1952-60; Ghirlando et al., (1999) *Immunol Lett* 68:47-52) or circular dichroism (Murray et al., (2002) *J. Chromatogr Sci* 40:343-9).

In a further embodiment, antibodies and antigen-binding fragments thereof (e.g., RB1) are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies (e.g., RB1) and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

Antibody Conjugates

The anti-hRSV F-protein antibodies and antigen-binding fragments thereof disclosed herein (e.g., RB1) may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein (e.g., RB1) may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antibodies and antigen-binding fragments disclosed herein (e.g., RB1) may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., European Patent Application Nos. EP 0 154 316 and EP 0 401 384.

The antibodies and antigen-binding fragments disclosed herein (e.g., RB1) may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention (e.g., RB1) may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibodies and antigen-binding fragments thereof of the invention (e.g., RB1) to the various moieties may be employed, including those methods described by Hunter et al., 1962, *Nature* 144:945; David et al., 1974, *Biochemistry* 13:1014; Pain et al., 1981, *J. Immunol. Meth.* 40:219; and Nygren, 1982, *Histochem. and Cytochem.* 30:407. Methods for conjugating antibodies and fragments are conventional and very well known in the art.

Prophylactic and Therapeutic Uses of Anti-hRSV Antibodies

Further provided are methods for preventing, treating or ameliorating a symptom of RSV infection in subjects, including human subjects, in need of such prevention, treatment, or amelioration with the isolated antibodies or antigen-binding fragments thereof disclosed herein (e.g., RB1). In one embodiment of the invention, such subject suffers from a RSV infection. In one embodiment of the invention, such subject is at risk of a RSV infection.

In a specific embodiment, a mammal, preferably a human, is administered a prophylactic, therapeutic or pharmaceutical composition comprising one or more antibodies of the present invention or fragments thereof for the treatment, prevention or amelioration of one or more symptoms associated with a RSV infection in an amount effective for decreasing RSV titers. In accordance with this embodiment, an effective amount of antibodies or antibody fragments reduces the RSV titers in the lung as measured, for example, by the concentration of RSV in sputum samples or a lavage from the lungs from a mammal. In another embodiment, a mammal, preferably a human, is administered a prophylactic, therapeutic or pharmaceutical composition comprising one or more antibodies of the present invention or fragments thereof for the treatment, prevention or amelioration of symptoms associated with a RSV infection in an amount effective for neutralizing RSV and/or blocking RSV infection in the mammal.

The monoclonal antibodies or antigen binding fragments thereof can also be used immunotherapeutically for RSV disease in both humans and other animals. The term, "immunotherapeutically" or "immunotherapy" as used herein in conjunction with the monoclonal antibodies or antigen binding fragments thereof of the invention denotes both prophylactic as well as therapeutic administration and both passive immunization with substantially purified polypeptide products, as well as gene therapy by transfer of polynucleotide sequences encoding the product or part thereof. Passive immunization includes transfer of active humoral immunity or providing antibodies to a subject in need thereof. Accordingly, in certain embodiments of the invention, the present invention provides methods for transfer of active humoral immunity and methods of providing RSV antibodies or antigen binding fragments thereof, such as IgG antibodies, to a patient at risk of RSV infection. Thus, the monoclonal antibodies or antigen binding fragments thereof can be administered to high-risk subjects in order to lessen the likelihood and/or severity of RSV disease or administered to subjects already evidencing active RSV infection.

The present invention also provides a method for modulating or treating at least one adult or pediatric RSV related disease, in a cell, tissue, organ, animal, or patient including, but not limited to, lower respiratory infections, pneumonia, tracheobronchitis, bronchiolitis, bronchitis, and any related infections or inflammatory disorders, such as but not limited to at least one of, or at least one inflammation related to, systemic inflammatory response syndrome, sepsis syndrome, gram positive sepsis, gram negative sepsis, culture negative sepsis, fungal sepsis, neutropenic fever, urosepsis, meningococcemia, adult respiratory distress syndrome, allergic rhinitis, perennial rhinitis, asthma, systemic anaphalaxis, receptor hypersensitivity reactions, chronic obstructive pulmonary disease (COPD), hypersensitivity pneumonitis, granulomas due to intracellular organisms, drug sensitivity, cachexia, cystic fibrosis, neonatal chronic lung disease; at least one infectious disease in a cell, tissue, organ, animal or patient, including, but not limited to, at least one of: acute or chronic bacterial infection, acute and chronic parasitic or infectious processes, including bacterial, viral and fungal infections, HIV infection, HIV neuropathy, meningitis, hepatitis (A,B or C, or the like), septic arthritis, peritonitis, pneumonia, epiglottitis, *E. coli* 0157:h7, hemolytic uremic syndrome, thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis, epididimitis, legionella, lyme disease, influenza A, Epstein-Barr virus, vital-associated hemaphagocytic syndrome, vital encephalitis, aseptic meningitis, and the like. Such a method can optionally comprise administering an effective amount of a composition or pharmaceutical composition comprising at least one RSV antibody or antigenic fragment thereof to a cell, tissue, organ, animal or patient in need of such modulation, treatment or therapy.

In one embodiment, prophylactic, therapeutic or pharmaceutical compositions comprising antibodies of the invention or fragments thereof are administered to a mammal, preferably a human, to treat, prevent or ameliorate one or more symptoms associated with RSV infection. In another embodiment, prophylactic, therapeutic or pharmaceutical compositions comprising antibodies of the invention or fragments thereof are administered to a human with cystic fibrosis, bronchopulmonary dysplasia, congenital heart disease, congenital immunodeficiency or acquired immunodeficiency, or to a human who has had a transplant (e.g., bone marrow, lung, or hematopoietic stem cell transplantation (HSCT)) to treat, prevent or ameliorate one or more symptoms associated with RSV infection.

In another embodiment, prophylactic, therapeutic or pharmaceutical compositions comprising antibodies of the invention or fragments thereof are administered to a human infant, preferably a human infant born prematurely or a human infant at risk of hospitalization for RSV infection to treat, prevent or ameliorate one or more symptoms associated with RSV infection. In yet another embodiment, prophylactic, therapeutic or pharmaceutical compositions comprising antibodies of the invention or fragments thereof are administered to the elderly or people in group homes (e.g., nursing homes or rehabilitation centers) or immunocompromised individuals.

It is preferred to use high affinity and/or potent in vivo inhibiting antibodies and/or neutralizing antibodies or antigen binding fragments thereof that immunospecifically bind to a RSV antigen, for both prevention of RSV infection and therapy for RSV infection. It is also preferred to use polynucleotides encoding high affinity and/or potent in vivo inhibiting antibodies and/or neutralizing antibodies or antigen binding fragments thereof that immunospecifically bind to a RSV antigen, for both prevention of RSV infection and therapy for RSV infection. Such antibodies or fragments thereof will preferably have an affinity for the RSV F glycoprotein and/or fragments of the F glycoprotein.

Antibodies and functional equivalents (such as antigen binding fragments thereof) according to the present invention recognize an epitope within RSV F protein. Antibodies or functional equivalents thereof that specifically recognize said epitope can be combined with RSV-specific antibodies that bind to a different epitope that are already known, such as palivizumab, D25, AM14, AM16 and AM23. By combining an antibody or functional equivalent according to the invention that specifically recognizes said epitope with a known RSV-specific antibody, two or more different epitopes of RSV are recognized during the same therapy. This way, a stronger immunogenic response to RSV and/or a higher antibody specificity against RSV can be reached. With a stronger immunogenic response to and higher specificity against RSV, such combination may result in more effective treatment and/or prevention of a RSV-related disorder.

One or more antibodies of the present invention or fragments thereof that immunospecifically bind to one or more RSV antigens may be used locally or systemically in the body as a prophylactic. The antibodies of this invention or fragments thereof may also be advantageously utilized in combination with other monoclonal or chimeric antibodies, or with lymphokines or hematopoietic growth factors (such as, e.g., IL-2, IL-3, IL-7, and IL-15), which, for example, serve to increase the number or activity of effector cells which interact with the antibodies. The antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the immune response. The antibodies of this invention or fragments thereof may also be advantageously utilized in combination with one or more drugs used to treat RSV infection such as, for example anti-viral agents.

Antibodies of the invention or fragments may be used in combination with one or more of the following drugs: NIH-351 (Gemini Technologies), recombinant RSV vaccine (Aviron), RSVf-2 (Intracel), F-50042 (Pierre Fabre), T-786 (Trimeris), VP-36676 (ViroPharma), RFI-641 (American Home Products), VP-14637 (ViroPharma), PFP-1 and PFP-2 (American Home Products), RSV vaccine (Avant Immunotherapeutics), and F-50077 (Pierre Fabre).

The antibodies or antigen binding fragments thereof of the invention may be administered alone or in combination with other types of treatments (e.g., hormonal therapy, immunotherapy, and anti-inflammatory agents). Generally, administration of products of a species origin or species reactivity (in the case of antibodies) that is the same species as that of the patient is preferred. Thus, in a preferred embodiment, human or humanized antibodies, fragments derivatives, analogs, or nucleic acids, are administered to a human patient for therapy or prophylaxis.

A "subject" may be a mammal such as a human, dog, cat, horse, cow, mouse, rat, monkey (e.g., cynomolgous monkey, e.g., *Macaca fascicularis*) or rabbit. In preferred embodiments of the invention, the subject is a human subject.

In particular embodiments, the antibodies or antigen-binding fragments thereof disclosed herein (e.g., RB1) may be used alone, or in association with antiviral therapy.

In particular embodiments, the antibodies or antigen-binding fragments thereof disclosed herein (e.g., RB1) may be used alone, or in association with another RSV monoclonal antibody.

In particular embodiments, the antibodies or antigen-binding fragments thereof disclosed herein (e.g., RB1) may be used alone, or in association with another RSV vaccine.

The term "in association with" indicates that the components administered in a method of the present invention (e.g., an anti-hRSV antibody or antigen-binding fragment thereof (e.g., RB1) along with, e.g., palivizumab) can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Experimental and Diagnostic Uses

The anti-hRSV F protein antibodies and antigen-binding fragments thereof disclosed herein (e.g., RB1) may be used as affinity purification agents. In this process, the anti-hRSV F protein antibodies and antigen-binding fragments thereof are immobilized on a solid phase such a Sephadex®, glass or agarose resin or filter paper, using methods well known in the art. The immobilized antibody or fragment is contacted with a sample containing the hRSV F protein (or a fragment thereof) to be purified, and thereafter the support is washed with a suitable solvent that will remove substantially all the material in the sample except the hRSV F protein, which is bound to the immobilized antibody or fragment. Finally, the support is washed with a solvent which elutes the bound hRSV F protein (e.g., protein A). Such immobilized antibodies and fragments form part of the present invention.

Further provided are antigens for generating secondary antibodies which are useful for example for performing Western blots and other immunoassays discussed herein. In particular, polypeptides are disclosed which comprise the variable regions and/or CDR sequences of a therapeutic antibody disclosed herein (e.g., RB1) and which may be used to generate anti-idiotypic antibodies for use in specifically detecting the presence of the antibody, e.g., in a therapeutic context.

Anti-hRSV F protein antibodies and antigen-binding fragments thereof may also be useful in diagnostic assays for hRSV F protein, e.g., detecting its expression in specific cells, tissues, or serum. Such diagnostic methods may be useful in various disease diagnoses. The present invention includes ELISA assays (enzyme-linked immunosorbent assay) incorporating the use of an anti-hRSV F protein antibody or antigen-binding fragment thereof disclosed herein (e.g., RB1).

For example, such a method comprises the following steps:

(a) coat a substrate (e.g., surface of a microtiter plate well, e.g., a plastic plate) with anti-hRSV F protein antibody or antigen-binding fragment thereof;

(b) apply a sample to be tested for the presence of RSV F protein to the substrate;

(c) wash the plate, so that unbound material in the sample is removed;

(d) apply detectably labeled antibodies (e.g., enzyme-linked antibodies) which are also specific to the RSV F protein antigen;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

Detection of the label associated with the substrate indicates the presence of the hRSV F protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3H$) which can be detected by scintillation counter in the presence of a scintillant.

An anti-hRSV F protein antibody or antigen-binding fragment thereof of the invention (e.g., RB1) may be used in a Western blot or immune-protein blot procedure. Such a procedure forms part of the present invention and includes e.g.:

(1) optionally transferring proteins from a sample to be tested for the presence of hRSV F protein (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound hRSV F protein or a fragment thereof with an anti-hRSV antibody or antigen-binding fragment thereof of the invention.

Such a membrane may take the form of a nitrocellulose or vinyl-based (e.g., polyvinylidene fluoride (PVDF)) membrane to which the proteins to be tested for the presence of hRSV in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-hRSV antibody or fragment, the membrane is optionally blocked, e.g., with non-fat dry milk or the like so as to bind non-specific protein binding sites on the membrane.

(2) washing the membrane one or more times to remove unbound anti-hRSV F protein antibody or fragment and other unbound substances; and (3) detecting the bound anti-hRSV F protein antibody or fragment.

Detection of the bound antibody or fragment indicates that the hRSV protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-hRSV F protein antibodies and antigen-binding fragments thereof disclosed herein (e.g., RB 1) may also be used for immunohistochemistry. Such a method forms part of the present invention and comprises, e.g., (1) contacting a cell to be tested for the presence of hRSV F protein with an anti-hRSV F protein antibody or antigen-binding fragment thereof of the invention; and (2) detecting the antibody or fragment on or in the cell.

If the antibody or fragment itself is detectably labeled, it can be detected directly. Alternatively, the antibody or fragment may be bound by a detectably labeled secondary antibody which is detected.

Pharmaceutical Compositions and Administration

To prepare pharmaceutical or sterile compositions of the anti-hRSV F protein antibodies and antigen-binding fragments of the invention (e.g., RB 1), the antibody or antigen-binding fragment thereof is admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.). In one embodiment, antibodies or antigen binding fragments thereof of the present invention are diluted to an appropriate concentration in a histidine buffer pH 5-7, at 1-20 mM and NaCl or sucrose (e.g., 2-15% (w/v)) is optionally added for tonicity. Additional agents, such as polysorbate 20 or polysorbate 80, at 0.01 to 0.10% (w/v) may be added to enhance stability. A representative formulation is 10 mM L-Histidine, 7% (w/v) Sucrose, and 0.02% (w/v) polysorbate-80, pH 6.0.

Toxicity and therapeutic efficacy of the antibodies or antigen binding fragments thereof of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. Preferred modes of administration are intramuscular, intravenous and intranasal.

In particular embodiments, the anti-hRSV F protein antibodies or antigen-binding fragments thereof of the invention (e.g., RB1) can be administered by an invasive route such as by injection. In further embodiments of the invention, an anti-hRSV F protein antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention (e.g., RB1) or a pharmaceutical composition thereof. The present invention also provides an injection device comprising any of the antibodies or antigen-binding fragments of the invention (e.g., RB1) or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

The administration regimen depends on several factors, including the serum or tissue turnover rate of the therapeutic antibody or antigen-binding fragment, the level of symptoms, the immunogenicity of the prophylactic/therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular prophylactic/therapeutic antibody and the severity of the condition being treated. Guidance in selecting appropriate doses of therapeutic antibodies or fragments is available (see, e.g., Wawrzynczak, (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al., 2003, *New Engl. J. Med.* 348:601-608; Milgrom et al., 1999, *New Engl. J. Med.* 341:1966-1973; Slamon et al., 2001, *New Engl. J.*

Med. 344:783-792; Beniaminovitz et al., 2000, *New Engl. J. Med.* 342:613-619; Ghosh et al., 2003, *New Engl. J. Med.* 348:24-32; Lipsky et al., 2000, *New Engl. J. Med.* 343:1594-1602).

Determination of the appropriate dose is made by the clinician, e.g., using parameters or factors known or suspected in the art to affect prevention or treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein (e.g., RB1) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al., 2003, *New Engl.* 1 Med. 349:427-434; Herold, et al., 2002, *New Engl. J. Med.* 346:1692-1698; Liu, et al., 1999, *J. Neurol. Neurosurg. Psych.* 67:451-456; Portielji, et al., 2003, *Cancer Immunol. Immunother.* 52:151-144). Doses may also be provided to achieve a predetermined target concentration of anti-hRSV antibody in the subject's serum, such as 0.1, 0.3, 1, 3, 10, 30, 100, 300 µg/ml or more. In other embodiments, an anti-hRSV antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-hRSV or antigen-binding fragment thereof of the invention (e.g., RB1) that, when administered alone or in combination with an additional therapeutic/prophylactic agent to a cell, tissue, or subject, is effective to neutralize RSV and/or prevent or cause a measurable improvement in one or more symptoms of disease or condition associated with RSV infection. An effective dose further refers to that amount of the antibody or fragment sufficient to result in at least partial prevention or amelioration of symptoms. When applied to an individual active ingredient administered alone, an effective dose refers to that ingredient alone. When applied to a combination, an effective dose refers to combined amounts of the active ingredients that result in the prophylactic or therapeutic effect, whether administered in combination, serially or simultaneously. In certain embodiments, an effective amount is an amount that provides a clinical target serum concentration of 10 µg/mL-30 µg/mL for 5 months. In one embodiment, an effective amount is a human dose that provides a Ctrough target of 10 µg/ml-30 µg/ml for efficacy, as determined in standard pre-clinical cotton rat models.

Kits

Further provided are kits comprising one or more components that include, but are not limited to, an anti-hRSV F protein antibody or antigen-binding fragment, as discussed herein (e.g., RB1) in association with one or more additional components including, but not limited to a pharmaceutically acceptable carrier and/or a prophylactic/therapeutic agent, as discussed herein. The antibody or fragment and/or the prophylactic/therapeutic agent can be formulated as a pure composition or in combination with a pharmaceutically acceptable carrier, in a pharmaceutical composition.

In one embodiment, the kit includes an anti-hRSV F protein antibody or antigen-binding fragment thereof of the invention (e.g., RB1) or a pharmaceutical composition thereof in one container (e.g., in a sterile glass or plastic vial) and a pharmaceutical composition thereof and/or a prophylactic/therapeutic agent in another container (e.g., in a sterile glass or plastic vial).

In another embodiment, the kit comprises a combination of the invention, including an anti-hRSV F protein antibody or antigen-binding fragment thereof of the invention (e.g., RB1) along with a pharmaceutically acceptable carrier, optionally in combination with one or more prophylactic/therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Prophylactic/Therapeutic Kits

As a matter of convenience, an anti-hRSV antibody or antigen-binding fragment thereof of the invention (e.g., RB 1) can be provided in a kit, i.e., a packaged combination of reagents in predetermined amounts with instructions for performing a diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-hRSV F protein antibody or antigen-binding fragment thereof packaged in a container, such as a vial or bottle, and further comprising a label attached to or packaged with the container, the label describing the contents of the container and providing indications and/or instructions regarding use of the contents of the container to prevent/treat one or more disease states as described herein.

In one aspect, the kit is for preventing or treating diseases/conditions associated with RSV infection and comprises an anti-hRSV F protein antibody or antigen-binding fragment thereof and a further prophylactic/therapeutic agent or a vaccine. The kit may optionally further include a syringe for parenteral, e.g., intravenous, administration. In another aspect, the kit comprises an anti-hRSV F protein antibody or antigen-binding fragment thereof and a label attached to or packaged with the container describing use of the antibody or fragment with the vaccine or further prophylactic/therapeutic agent. In yet another aspect, the kit comprises the vaccine or further prophylactic/therapeutic agent and a label attached to or packaged with the container describing use of the vaccine or further prophylactic/therapeutic agent with the anti-hRSV F protein antibody or fragment. In certain embodiments, an anti-hRSV F protein antibody and vaccine or further prophylactic/therapeutic agent are in separate vials or are combined together in the same pharmaceutical composition.

For combination prophylaxis or therapy, concurrent administration of two prophylactic/therapeutic agents does not require that the agents be administered at the same time or by the same route, as long as there is an overlap in the time period during which the agents are exerting their prophylactic/therapeutic effect. Simultaneous or sequential administration is contemplated, as is administration on different days or weeks.

The prophylactic/therapeutic and detection kits disclosed herein may also be prepared that comprise at least one of the antibody, peptide, antigen-binding fragment, or polynucleotide disclosed herein and instructions for using the composition as a detection reagent or prophylactic/therapeutic agent. Containers for use in such kits may typically comprise at least one vial, test tube, flask, bottle, syringe or other suitable container, into which one or more of the detection and/or prophylactic/therapeutic composition(s) may be placed, and preferably suitably aliquoted. Where a second prophylactic/therapeutic agent is also provided, the kit may also contain a second distinct container into which this second detection and/or prophylactic/therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or prophylactic/therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982, 1989 $2^{nd}$ Edition, and 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Single chain antibodies and diabodies are described (see, e.g., Malecki et al., 2002, *Proc. Natl. Acad. Sci. USA* 99:213-218; Conrath et al., 2001, *J. Biol. Chem.* 276:7346-7350; Desmyter et al., 2001, *J. Biol. Chem.* 276:26285-26290; Hudson and Kortt, 1999, *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2nd* ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1: Identification of a Fully Human RSV Neutralizing Antibody

In order to identify potent HRSV neutralizing antibodies, serum was obtained from donors under informed consent and assayed for the ability to neutralize HRSV virus in vitro. For the neutralization assay, serum samples were first serially diluted and then incubated with 600 pfu of a hRSV-A strain expressing the enhanced green fluorescent protein (RSV-GFP). The RSV-GFP was mixed 1:1 with serum dilutions in a total volume of 200 µl per well in 96-well U-bottom plates at 37° C. for 1 hr. 100 µl of the mixture per well was then transferred to HEp-2 cell seeded plates (15,000 cells per well). The plates were scanned on Acumen® Cellista (TTP LabTech, Cambridge, Mass.) and data were exported as number of GFP events and total fluorescence intensity per well. NT50 values were calculated using GraphPad Prism 6 (GraphPad Software, Inc., La Jolla, Calif.) by four parameter curve fitting. ELISA binding titers to RSV pre-F and post-F proteins were performed as per the following. Nunc C96 Maxisorp® Nunc-Immuno™ plates (Thermo Scientific, Inc.) were coated with 50 µl per well of hRSV pre-F (See McLellan et al., 2013, Science 342:592) or post-F protein (post-fusion F LZF21 protein consists of the wt F ectodomain without the fusion peptide (See McLellen et al., 2011, J. Virol 85:7788)) at 1 µg/ml in PBS at 4° C. overnight. The plates were washed with PBS/Tween 20 and then blocked with 3% non-fat milk in PBS. Afterwards, 50 µl of serially diluted serum samples were added per well and incubated at room temperature for 90 min. The plates were washed and HRP-conjugated goat anti-human IgG (SouthernBiotech, Birmingham, Ala.) was added at 1:2,000 dilution. One hour later, the plates were washed and developed with SuperBlu Turbo TMB solution (ViroLabs, Inc., Sterling, Va.). OD450 nm readings were obtained using a Wallac 1420 VICTOR²™ Multilabel Counter (Perkin Elmer, Waltham, Mass.). EC50 values were calculated using GraphPad Prism 6 by four parameter curve fitting. A subset of the donors that demonstrated high HRSV neutralizing and binding titers were recalled to procure larger blood volumes for PBMC generation. PBMC preparation was carried out by a commercial vendor and the purchased PBMC's were stored at liquid nitrogen until further use.

PBMC's from one subject demonstrated good neutralization titers and had also the highest titers in a ELISA binding assay to Post Fusion F protein as well as being one of the elite binders to pre-Fusion F protein (data not shown).

Therefore, this donor's PBMCs were chosen to isolate Post-F specific memory B-cells by FACS sorting.

Biotinylated trimeric post-fusion F protein (LZF21) was prepared by biotinylating LZF21 (McLellen et al., 2011, J. Virol 85:7788) using E-Z Link™ Sulfo-NHS-LC biotinylation kit (Life Technologies, Grand Island, N.Y.) according to the manufacturer's instructions. The LZF21 protein consists of the wild-type F protein ectodomain without the fusion peptide (McLellen et al., 2011, J. Virol 85:7788). The fusion F protein specific murine hybridoma 4D7 (4D7 is a mouse hybridoma that was generated by immunizing Balb/c mice with RSV A2 virus). Balb/c mice were immunized twice, intraperitoneally, with RSV A2 virus and boosted three days prior to fusion, using 20 µg of purified RSV A2 (Advanced Biotechnologies, Inc., Columbia, Md.), by intravenous injection. The spleen was harvested and splenocytes were fused with SP2/0 myeloma cells using polyethylene glycol. Cells were added to Medium D (StemCell Technologies Inc., Vancouver, BC), plated in 245 mm×245 mm square petri dishes and incubated at 37° C., 5% $CO_2$ for 2 weeks. Individual colonies were picked using a ClonePix (Genetix), transferred to 96 well plates and incubated as above for 1 week. Supernatants were then screened for anti-RSV activity by ELISA against purified RSV A2. Positive clones, including 4D7, were expanded and further sub-cloned by limiting dilution. Sub-clones were screened as described above and 4D7-8 was identified and used to optimize the staining of LZF21-biotin to memory B-cells by FACS (data not shown). Through these optimization experiments, it was determined that 1.5 µg/ml of LZF21-biotin was the best concentration for staining of post-F specific memory B-cells. The specificity of the staining reaction was demonstrated by using an irrelevant murine hybridoma as a negative control and competing the binding with 100-1000× excess of unlabeled LZF21.

Antigen specific memory B-cells were delineated as $CD3^-CD19^+IgG^+LZF21^+$. These cells were sorted into a 96 well plates (one cell/well) containing a CD40 ligand expressing HEK293 cell line (made using standard molecular biology techniques) and IL-21 (Sino Biological Inc., North Wales, Pa.). Out of 30 sorted samples, the supernatant from 6 wells demonstrated binding to post-F protein in an ELISA assay (performed as described above). These samples also bound to pre-F protein (data not shown). These six samples were then tested in neutralization assay, as described above, without dilution. The presence of neutralization activity was determined based on the reduction of GFP events. Among six samples, two of them (designated RB1 and RB11) showed complete neutralization of HRSV-A strain (See Table 3).

TABLE 3

| Well ID | ELISA 450 nm | | | Neutralization | |
| --- | --- | --- | --- | --- | --- |
| | IgG | Post F | Pre-F | GFP Object# | % Neut |
| A8 | 0.641 | 1.743 | 1.222 | 783 | |
| A9 | 1.743 | 1.915 | 1.754 | 689 | |
| A11 | 1.81 | 1.905 | 1.555 | 500 | |
| B1 | 1.82 | 1.925 | 1.910 | 0 | 100% |
| B11 | 1.851 | 1.748 | 1.900 | 1 | 100% |
| B12 | 1.801 | 1.838 | 1.679 | 548 | |
| Control | 0.037 | 0.038 | 0.044 | 596 | |

RNA Extraction and RT-PCT for Single-Sorted Memory B Cell Culture

Part 1:

The RNA from a 96 well plate from RB1 hit lysate was extracted using a RNeasy® Micro Kit (Qiagen, Inc., Valencia, Calif.) as per the manufacturer's manual. The RNA concentration was determined with NanoDrop™ 2000C (Thermo Fisher Scientific Inc., Wilmington, Del.) under UV 260 nm. The extracted RNA from the RB1 well was used as template in the RT-PCR amplification of antibody heavy and light chain genes using primer sequences using sequences from the leader sequence (forward) and C' end of IgG JH, Kappa constant region or Lambda constant region (reverse).

OneStep RT-PCR kit (Qiagen Inc, Valencia, Calif.) was used according to the manufacturer's instructions to amplify the antibody sequences. The PCR conditions were as follows: 50° C. for 30 mins, 95° C. for 15 mins, [94° C. for 30 sec, 55° C. for 30 sec, 72° C. for 1 min]×40, 72° C. for 10 min, and 4° C. hold.

The RT-PCR product was directly used as a template for nested PCR.

Part 2: Nested PCR

The RT-PCR products were used as templates in nested-PCR to amplify antibody variable regions with pfx50 DNA polymerase (Invitrogen, catalog no: 12355-012). The design for nested-PCR primers was based on germline sequences of framework 1 region of human IgG heavy and light chain variable regions.

1 µl RT-PCR product was mixed with 2.5 µl 10×PCR buffer, 2.5 µl 10×PCRX Enhancer (Invitrogen), 0.5 µl dNTP mix, 0.5 µl forward primer pool (10 µM each), 0.5 µl reverse primer (10 µM), 0.5 µl pfx50 DNA polymerase and 17 µl water. Nested PCR condition was: 2 min at 94° C., 10 cycles of 94° C. for 30 sec, 50° C. for 30 sec, 68° C. for 1 min, followed by 30 cycles of 94° C. for 30 sec, 60° C. for 30 sec, 68° C. for 1 min, then 7 min elongation at 68C, followed by 4° C. hold for short term storage.

The RB1 nested PCR products of VH and VK or VH and VL amplified PCR products were used as template in the overlap PCR with specific linkers for annealing antibody light and heavy chain genes together to facilitate the next step infusion cloning.

Part 3. Overlap PCR and Infusion Cloning pfx50 DNA polymerase (Invitrogen) was used in this reaction. Forward and reverse primers were designed to facilitate the infusion cloning of overlap PCR products into a cloning vector. 1 µl heavy chain nested PCR product, 1 µl light chain nested PCR product and 1 µl linker were mixed with 5 µl 10×PCR buffer, 5 µl 10×PCRX enhancer, 1 µl dNTP mix, 1 µl forward primer (10 µM), 1 µl reverse primer (10 µM), 1 µl pfx50 DNA polymerase and 33 µl water.

PCR conditions were as follows: 94° C. for 2 mins, [94° C. for 30 sec, 60° C. for 30 sec, 68° C. for 2 min]×10, [94° C. for 30 sec, 65° C. for 30 sec, 68° C. for 2 min]×30, 68° C. for 7 min, 4° C. hold.

The overlap PCR products were agarose gel purified for infusion cloning (a RB1 VH+VK overlap PCR product of around 1.2 kb was obtained). The RB1 VH+VK overlap PCR products were cloned into pMab11Exp2 (with OmpA leader sequence for light chain expression, with PelB leader sequence for heavy chain expression) vector with the application of infusion cloning. Infusion HD® cloning Kit (Clontech Laboratories, Inc., Mountain View, Calif.) was used and the manufacturer's instructions were followed. Transformants were picked and sent to GeneWiz, Inc. (South Plainfield, N.J.) for sequencing.

The sequencing results were analyzed with Sequencher (Gene Codes Corporation, Ann Arbor, Mich.).

The nucleotide and amino acid sequences of RB1 are depicted in Table 7 (the patient isolated RB1 variable heavy chain and variable light chain amino acid sequences are represented by SEQ ID NO: 9 and SEQ ID NO: 8, respectively). Due to the design of the Jh reverse primers having a nucleotide change, an isoleucine present in the natural sequence at position 125 was changed to threonine in the expressed protein (the resulting RB1 variable heavy chain is represented by SEQ ID NO: 7). Amino acid sequences of RB1 antibody heavy and light chain variable domain genes were sent to GenScript USA, Inc. (Piscataway, N.J.) for codon optimization and human IgG1 conversion and CHO transient expression and production. Synthesized DNAs were subcloned into pTT5 vector for CHO-3E7 cell expression. The recombinant plasmids encoding heavy and light chains of each antibody were transiently co-transfected into CHO-3E7 cell cultures. The cell culture supernatants collected on day 6 were used for purification through Protein A column. Purified RB1 human IgG1 was used in neutralization assay and other characterization experiments as described in Example 2.

Example 2: Characterization of Anti-hRSV Antibodies

Figure 1B:
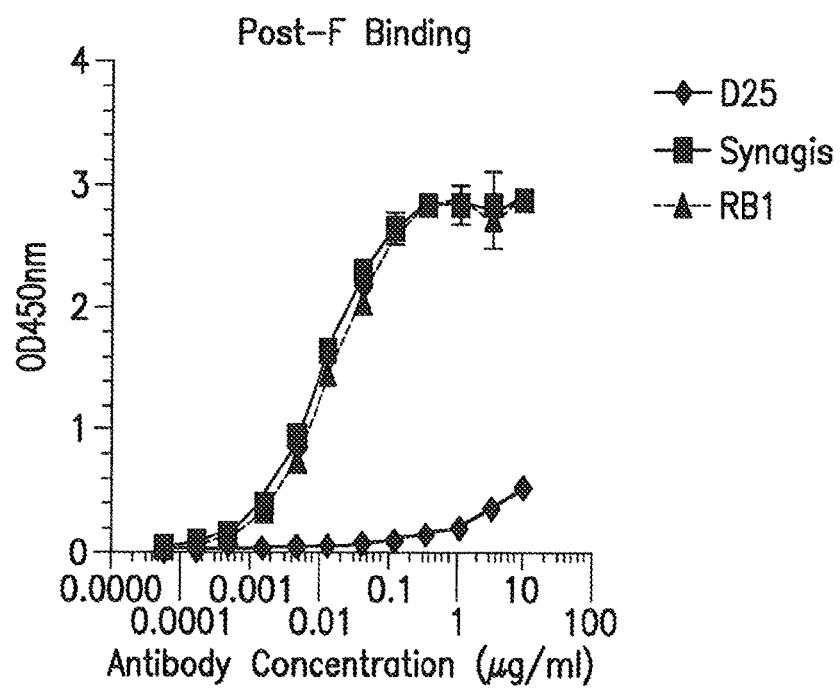

RB1 bound to both Pre F and post fusion F protein in an ELISA assay as described in Example 1 with an $EC_{50}$ ranging from 1-10 ng/ml, whereas the D25 antibody (See Kwakkenbos et al., 2010, *Nature Medicine* 16:123-128) bound preferentially to pre-fusion F. See FIGS. 1A-B.

| mAb ID | Pre-F (EC50 ng/ml) | Post-F (EC50 ng/ml) |
| --- | --- | --- |
| D25 | 8.939 | >10,000 |
| palivizumab | 17.37 | 10.5 |
| RB1 | 7.053 | 14.08 |

Neutralization for RB1, RB 11, and some benchmark antibodies reported in the literature (D25, palivizumab, full length [D25 antibody was made in house based on the published sequence and SYNAGIS® (palivizumab) was purchased from Myoderm, Norristown, Pa.]) was compared in RSV A Long strain (ATCC Number VR-26™) and RSV B Washington strain18537 strain (ATCC Number VR-1580™). The test samples were three-fold serially diluted in EMEM supplemented with 2% heat inactivated FBS, for eleven dilution points. The serially diluted samples were then mixed with equal volumes of EMEM supplemented with 2% heat inactivated FBS containing 100 pfu/well of RSV A or B strains. After incubation at 37° C. for 1 hr, 100 µl of HEp-2 cells at a concentration of $1.5 \times 10^5$ cells/ml was transferred to the 96 well plates containing the virus/antibody mixture. At 3 days post infection, the cells were washed once with PBS and then fixed in 80% acetone for 10 min at room temperature. A mixture of RSV F (mAb143-F3-B138) and RSV N (34C9) specific mouse mAbs (obtained in-house) was added to the plates and incubated for 1 hour at room temperature. Plates were washed with PBS/0.05% Tween 20 and biotinylated horse anti-mouse IgG was added to the plates and incubated for 1 hour at room temperature. Plates were washed with PBS/0.05% Tween. Infrared dye-Streptavidin was used to detect RSV specific signal and two cell stains for assay normalization were added to the 96-well plates and incubated for 1 hour in the dark. Following 1 hour incubation, the plates were washed, air dried for 20 minutes in the dark and read on the Licor Aerius® Automated Imaging System utilizing a 700 channel laser for cell normalization and an 800 channel laser for detection of RSV specific signal. 800/700 ratios and percent neutralization were calculated and IC50 values were determined by four parameter curve fit in GraphPad.

Figure 2A:
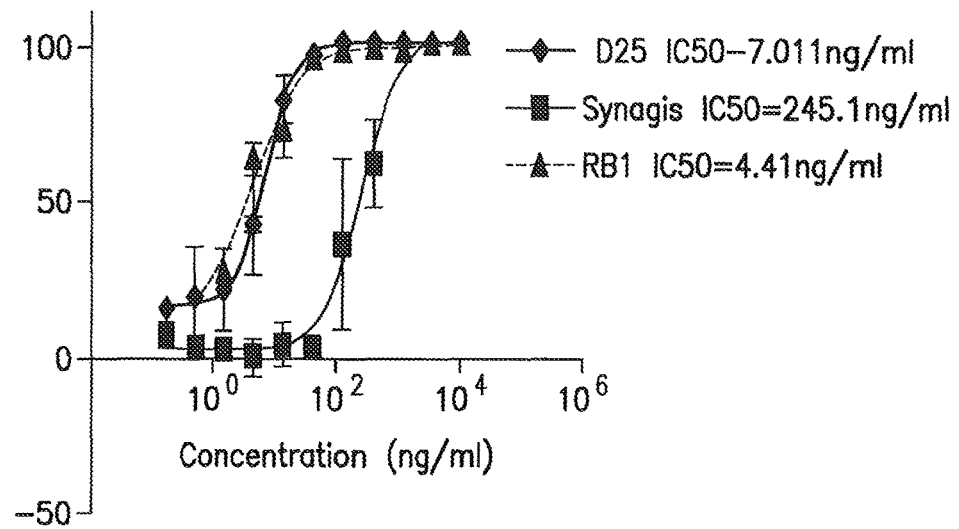
FIGS. 2A-B show neutralizing curves for human RSV antibodies in RSV A Long strain (A) and RSV B Washington strain (B).
Figure 2B:
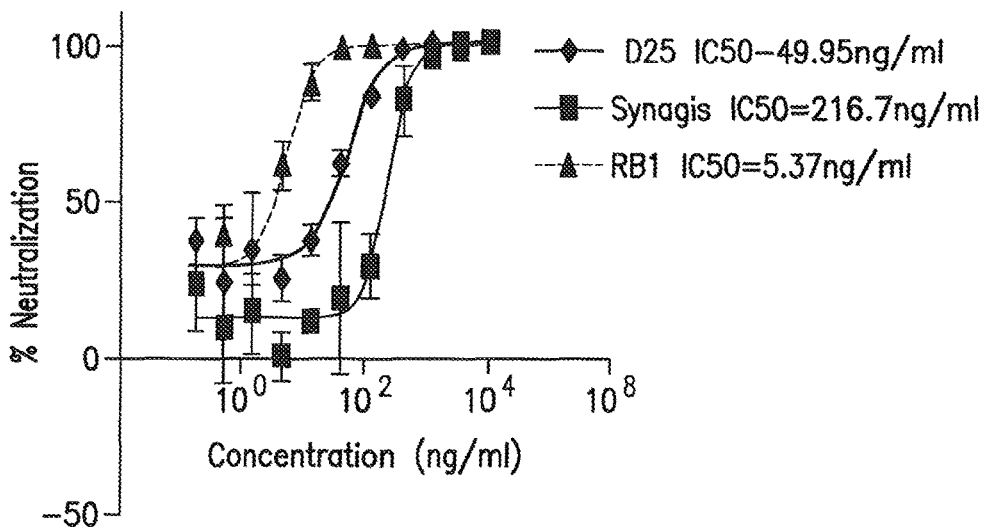

RB1 was able to neutralize the RSV-A and RSV-B strains with equal potency (IC50 of 1-5 ng/ml). RB1 also demonstrated superior anti-RSV neutralization compared to the benchmark antibodies. See FIGS. 2A-B and Table 4.

TABLE 4

Binding and neutralization potency of RB1 compared to benchmark antibodies

| | Pre-fusion F binding | Post-fusion F binding | Neutralizing Activity, IC50 (ng/mL) | |
| --- | --- | --- | --- | --- |
| | | | RSV A/ Long | RSV B/ washington |
| RB1 | + | + | 3 | 1.7 |
| D25 | + | − | 3.6 | 25.9 |
| AM22 | + | − | 50 | 172.8 |
| 131-2A, mouse (Millipore) | +/− | + | 1046 | >10,000 |
| 4D7 (Merck), mouse | +/− | + | 2408 | >10,000 |
| palivizumab | + | + | 211.5 | 166 |
| MPE8 | + | − | 106.6 | 46 |
| 101F, mouse | + | + | 67 | 43.6 |
| AM14 | + | − | 3.2 | 1.9 |

Affinity determination for binding of RB1 for pre- and post-fusion F protein: The kinetic binding activity of anti-human RSV F protein antibody RB1 (made as described in Example 1) was measured by surface plasmon resonance using a Biacore T200 system (Biacore, GE Healthcare, Piscataway, N.J.). Approximately 5000 RU of Anti-mouse IgG, GE Healthcare Catalog Number BR-1008-38, or approximately 13,000 RU of Goat Anti-Rat IgG Fc gamma, Fragment Specific, Jackson ImmunoResearch Catalog Number 112-006-071, was immobilized via amine coupling chemistry onto a Series S CM5 sensor chip, catalog number BR-1005-30.

Background subtraction binding sensorgrams were used for analyzing the rate constant of association ($k_a$) and dissociation ($k_d$), and the equilibrium dissociation constant $K_D$. The resulting data sets were fitted with a 1:1 Langmuir Binding Model using the Biacore T200 evaluation software (version 2.0). Table 5 summarizes the affinities for the anti-human RSV F protein antibody to the pre-fusion and post-fusion forms of the RSV F protein.

TABLE 5

Measurement of Affinity for RB1 to RSV pre-fusion F and post-fusion F using BIAcore

| Protein | $K_{on}$ (M − 1 S − 1) | $K^{Off}$ (S − 1) | $K_D$ (nM) |
| --- | --- | --- | --- |
| pre-Fusion F | $4.4 \times 10^6$ | $1.4 \times 10^{-4}$ | 0.031 |
| Post-Fusion F | $2.2 \times 10^6$ | $9 \times 10^{-4}$ | 0.41 |

RB1 is a very potent binder of pre-fusion F protein with a Kd of ~31 pM. The Kd for post fusion binding was a magnitude lower at 0.41 nM. The Kd for D25 as reported in International Patent Application Publication No. WO2014121021 A1 was 57 pM. Also the antibody RB1 stays on longer on pre-fusion F than post as seen with a slower off rates of $1.4 \times 10^{-4}$ as compared to post Fusion F protein.

Example 3: Epitope Mapping of RB1 Antibody

Figure 3A:
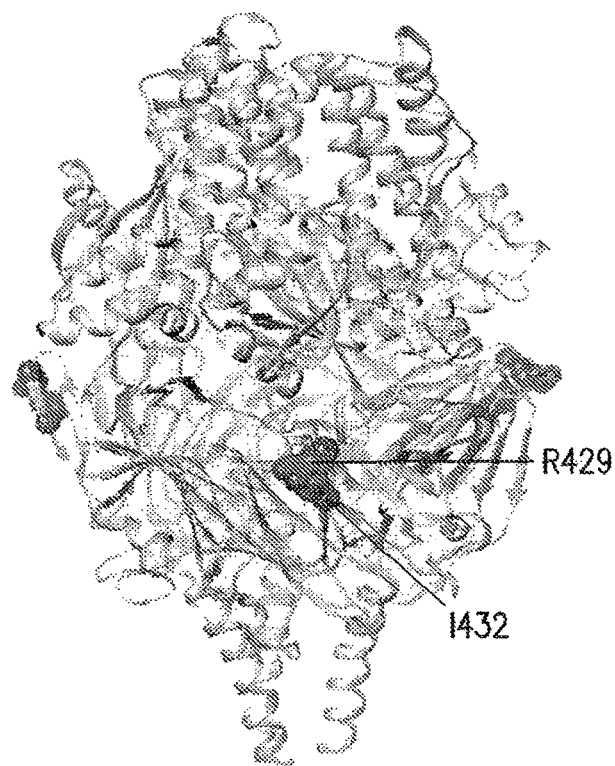
FIGS. 3A-B show epitope mapping of RB1 by alanine scanning mutagenesis of Fusion F protein (A) and epitope mapped residues on Pre-Fusion F crystal structure (B).
Figure 3B:
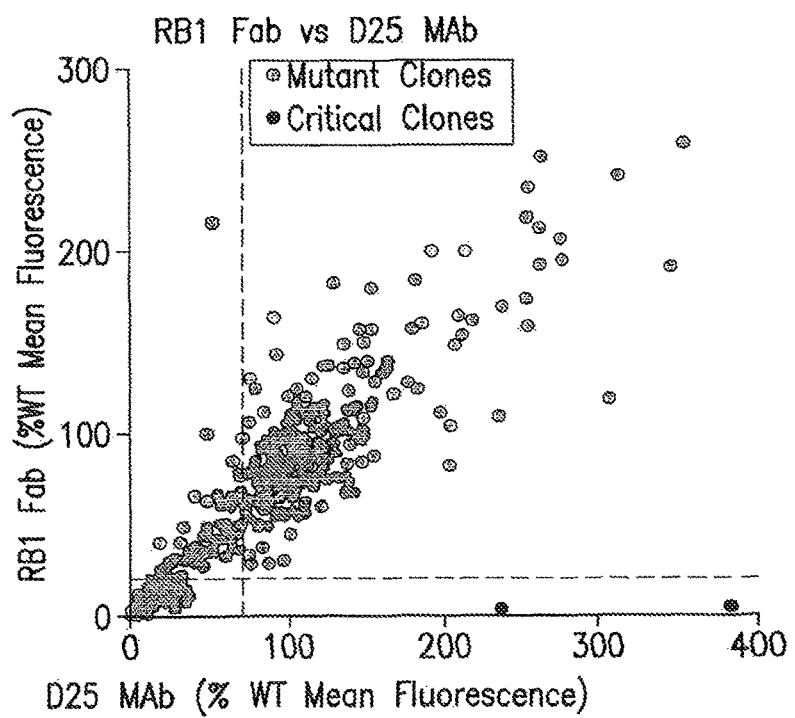
Figure 4A:
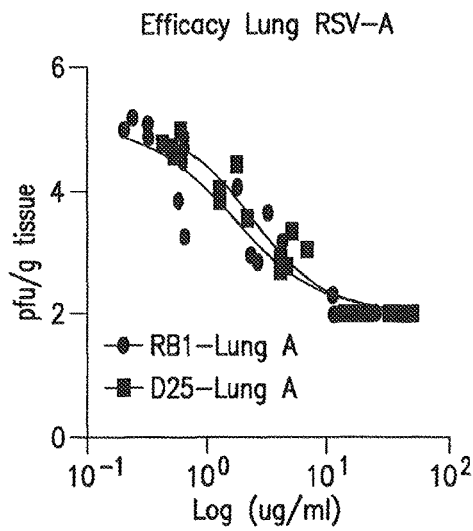
FIGS. 4A-D show the efficacy of RB1 compared to D25 in lungs in a cotton rat challenge model of RSV A plotted against concentrations of antibody (A) and RSV B challenge plotted against concentrations of antibody (B) or viral particles (PFU/g) present in the tissues plotted against dose of antibody for RSV A challenge (C) and RSV B challenge (D).
Figure 4B:
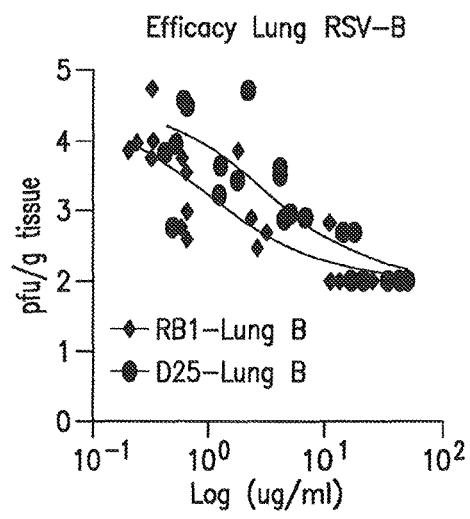
Figure 4C:
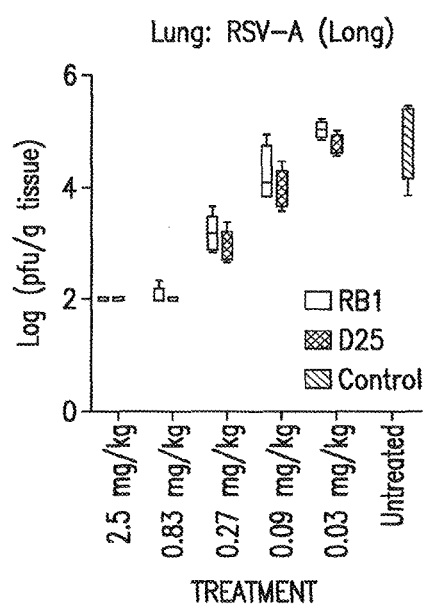
Figure 4D:
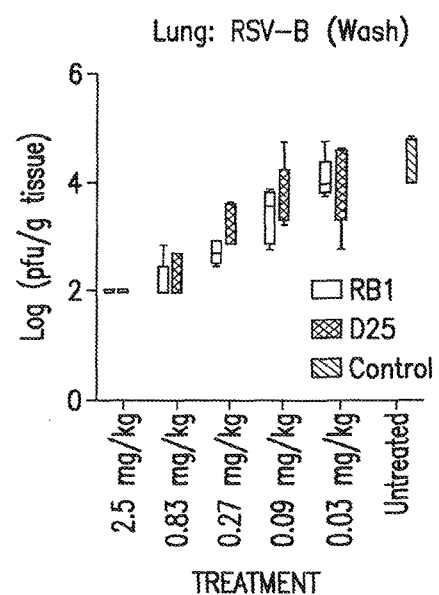
Figure 5A:
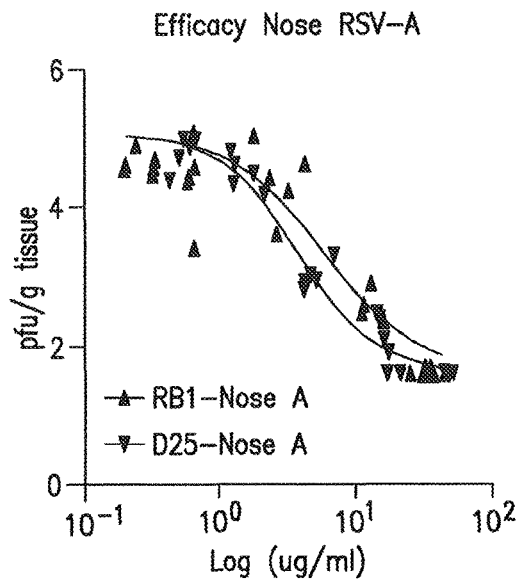
FIGS. 5A-D show the efficacy of RB1 compared to D25 in nose in a cotton rat challenge model of RSV A plotted against concentrations of antibody (A) and RSV B challenge plotted against concentrations of antibody (B) or viral particles (PFU/g) present in the tissues plotted against dose of antibody for RSV A challenge (C) and RSV B challenge (D).
Figure 5B:
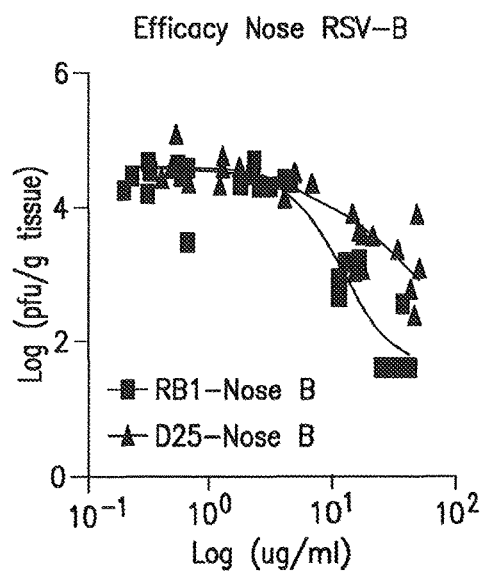
Figure 5C:
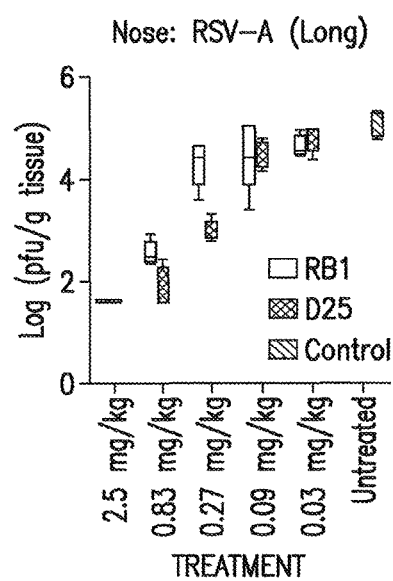
Figure 5D:
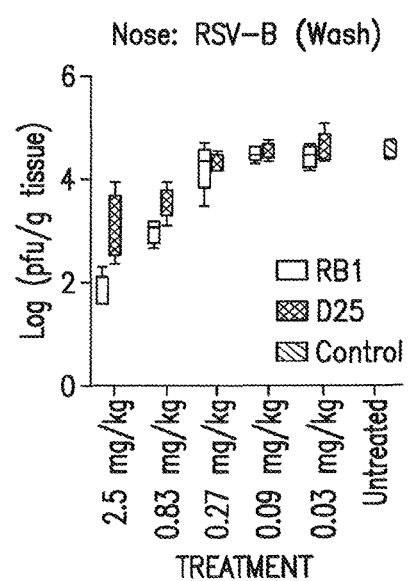

RB1's binding epitope on fusion F protein was mapped by carrying out an alanine scan mutagenesis experiment. Epitope mapping was performed by shotgun mutagenesis at Integral Molecular as described. (Davidson and Doranz, 2014, Immunology 143(1): 13-20). To construct a shotgun mutagenesis library, RSV-F protein expression vector is mutagenized to create a library of clones, each representing an individual point mutant and cumulatively covering all residues in the protein. Libraries were constructed using alanine scanning mutagenesis which provides a more controlled method of defining the side-chain contributions of each residue. Using semi-automated robotic protocols, each mutated plasmid was individually cloned, sequenced, miniprepped and arrayed in 384-well microplate format for repeated transfection, expression and antibody binding assays in human cells. Alanine scanning mutant library was screened against RB1 for loss of antibody binding. Two residues arginine-429 and Isoleucine-432 were identified as critical for RB1 binding. See below and FIG. 3A. RB1 appears to be a site IV mAb (101F-like) and Site IV binding antibodies in the literature have been reported to bind both pre-fusion and post-fusion F.

| | Binding Reactivity (% WT) | | |
|---|---|---|---|
| Mutation | RB1 MAb | RB1 Fab | D25 MAb |
| R429A | 33.1 (27) | 5.1 (4) | 385.0 (13) |
| I432A | 36.7 (39) | 3.6 (7) | 327.8 (161) |

We further co-crystalized RB1 Fab with pre-fusion F protein to understand better the binding epitope. Diffraction data were collected from crystals at 3.4-3.5 A°. The RB1 antibody binds to the pre-fusion F protein through interactions with the CDR loops of both heavy and light chains. The light chain CDR3 loop interacts with the side chain of Arg 429 through the formation of two hydrogen bonds between the carbonyl oxygens of Phe 91 and Leu 92 and the guanidino nitrogens of Arg 429. Also on the light chain, Asp 50 and Glu 55 on the CDR2 loop are positioned to form hydrogen bonds with Asn 426 and Lys 445 of RSV. Extensive interactions are made through the CDR3 loop of the heavy chain of RB1, with Tyr 104 and Tyr 110 forming a surface for van der Waals interaction with Ile 432 on RSV. Lys 433 of RSV forms a hydrogen bond with Asn 107 of the CDR3 loop. From the crystal structure, the light chain of RB1 also packs against Glu 161 and Ser 182 or the neighboring monomer of the RSV pre-fusion trimer.

The binding epitope that was identified for RB1 is highly conserved among 944 of 946 F protein sequences reported in the literature. This suggests that resistance to antibodies to this region would be expected to be low.

Example 4: Anti-RSV Activity of RSV Antibodies in Animal Model

RB1 antibody was compared to D25 and palivizumab for affording protection in the cotton rat challenge model. The study included palivizumab, D25 and RB1 antibodies given at 2.5 mg/k and serial diluted 10 fold to 0.25 mg/mk. In this model of passive immunotherapy, cotton rats were given RB1, D25 or palivizumab at various concentration at d0 and challenged with $10^5$ pfu of RSV one day later. The nose and the lung titers of challenged RSV virus were four days post challenge and used to determine viral shedding via a plaques assay.

Cotton Rat:

At least five cotton rats (*Sigmodon hispidus*), 3-7 weeks old with an average body weight of approximately 100 grams were obtained from SAGE Labs (Boyertown, Pa.). Conventional rodent chow and water were provided ad libitum.

Antibody Reagents:

Palivizumab 100 mg lyophilized (Myoderm, Norristown, Pa.) was formulated in water at 100 mg/ml. The other antibodies were expressed and purified in house.

Formulations of Antibody Reagents:

The formulation buffers were specific for each antibody to stabilize the proteins and prevent precipitation. The formulations were as follows: RB1 and D25 were diluted in 1× Phosphate Buffered Saline, pH 7.2. Palivizumab was formulated as per manufacturer suggestion by dissolving in distilled $H_2O$ which would effectively buffer the protein in 25 mM histidine and 1.3 mM glycine pH6.0.

Dosing Solution Preparation, Administration, and Analyses:

Five animals were randomly weighed to determine average weight of the cohorts used. Formulations were prepared about one hour prior to administration into the animals. Frozen stocks of antibodies were thawed on wet ice for a single thaw. Each antibody was diluted to the proper dose concentration to be delivered to each group. On day 0 (initiation of the study) animals that were randomly assigned to each group were lightly sedated with 1-4% isoflurane anesthesia and administered 0.1 ml into the right quadricep intramuscularly with a 26G syringe and needle. Animals recovered from the effects of the sedation within two minutes. About 24 hours later (+/−2 hours), cotton rats were sedated with 1-4% isoflurane, bled via the retroorbital plexus and then immediately dosed through the nares with 0.1 ml of $1 \times 10^{5.5}$ pfu of RSV A2 or RSV B Washington wild type virus in Williams E medium. Four days post inoculation, animals were sacrificed by $CO_2$ inhalation and lung (left lobes) and nasal turbinates were removed and homogenized in 10 volumes of Hanks Balanced Salt Solution (Lonza) containing Sucrose Phosphate Glutamine buffer (SPG) on wet ice. Samples were clarified by centrifugation at 2000 rpm for 10 minutes, aliquoted, flash frozen, and immediately stored frozen at −70° C. until tested in plaque assay.

As depicted in FIGS. 4A-D and FIGS. 5A-D, RB1 was able to achieve 2-3 log reduction in virus titers for both RSV A and RSV B in lung and nose at a dose of 2.5 mpk dose similar to D25 but better than palivizumab which was unable to impact the virus titers in the nose.

Example 5: Fc Engineering of RB1

The neonatal Fc receptor for IgG (FcRn) has been well characterized in the transfer of passive humoral immunity from a mother to her fetus. In addition, throughout life, FcRn protects IgG from degradation, thereby explaining the long half-life of this class of antibody in the serum. See, e.g., Israel et al., 1996, Immunology 89:573-8. FcRn binds to the Fc portion of IgG at a site that is distinct from the binding sites of the classical FcγRs or the C1q component of complement. The FcRn-Fc co-crystal structure revealed that FcRn binds to the CH2-CH3 hinge region of IgG antibodies.

A distinguishing characteristic of the IgG-FcRn pathway is obligate pH dependence. IgG-FcRn binding is driven by acidic pH (6.0) in the lysosome, whereas disassociation occurs at the neutral pH (7.4) of the extracellular environment. Acidification (pH 6.0-6.5) in the lysosomes enables the binding of FcRn to the Fc region of IgG with a low micromolar affinity and protects it from catabolism. The protected FcRn-bound IgG is subsequently shuttled to the cell surface and released into the extracellular environment. This process protects antibodies by decreasing their exposure to extracellular degradation.

The RB1 antibody was subjected to Fc Engineering in an effort to improve half-life. RB1+YTE is a derivative of RB1 with the triple mutation (M252Y/S254T/T256E (YTE)) introduced into the Fc portion of RB1. This YTE mutation set improves antibody binding to neonatal Fc receptors leading to longer half lives in humans. See, e.g., Dall'Acqua et al., 2006, J Biol Chem. 281:23514-24. Mutations in 3 amino acids (YTE: M252Y/S254T/T256E) within the Fc region of motavizumab has led to a 10-fold increase in in vitro FcRn binding at pH 6.0 for both humans and monkeys consequently resulting in a 4-fold increase in in vivo serum half-life in monkeys. See Robbie et al., 2013, Antimicrob Agents Chemother. 57:6147-53.

Amino acid sequences of RB1+YTE antibody heavy and light chain variable domains were sent to GenScript USA, Inc. (Piscataway, N.J.) for codon optimization and human IgG1 conversion and CHO transient expression and production. The nucleotide and amino acid sequences of RB1+YTE are depicted in Table 7.

Synthesized DNAs were subcloned into pTT5 vector for CHO-3E7 cell expression. The recombinant plasmids encoding heavy and light chains of each antibody were transiently co-transfected into CHO-3E7 cell cultures. The cell culture supernatants collected on day 6 were used for purification through Protein A column. Purified RB1+YTE human IgG1 was used in a neutralization assay and other characterization experiments.

Example 6: Characterization of RB1+YTE

Figure 6:
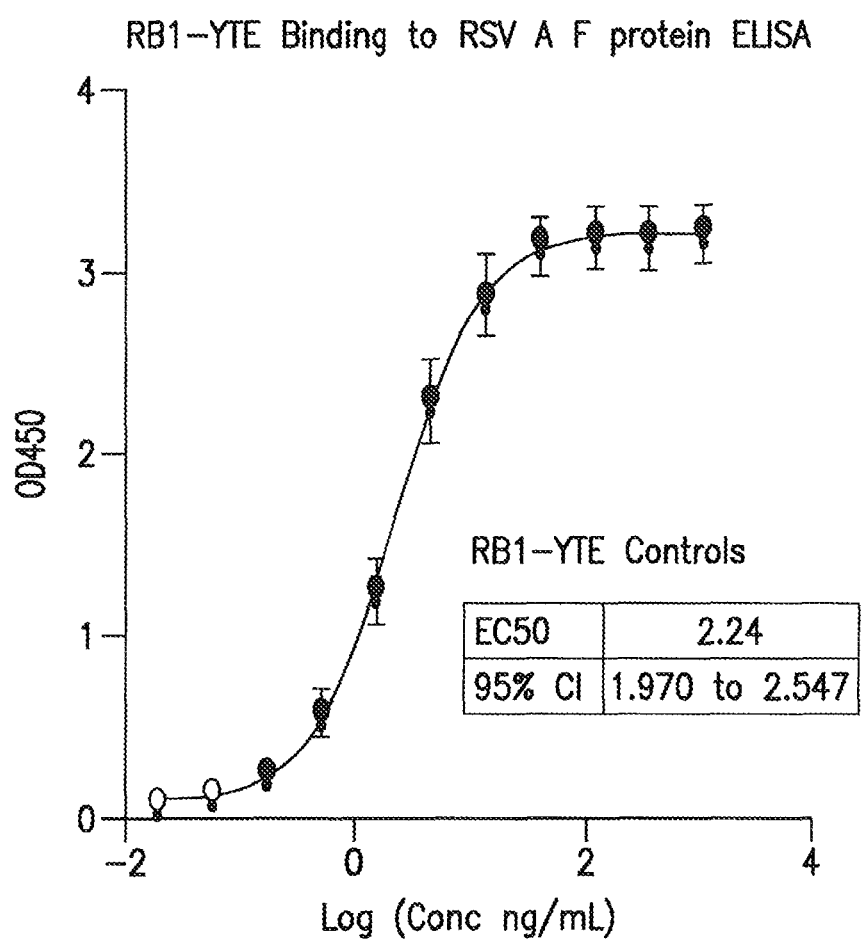
FIG. 6 shows a binding curve (from ELISA) of human RSV antibody RB1+YTE to human RSV A F protein.

RB-1+YTE bound to F protein in an ELISA assay performed as described in Example 1 with an $EC_{50}$ ranging from 1.97 to 2.457 ng/ml. See FIG. 6. Neutralization for RB1+YTE, and a benchmark antibody reported in the literature (Motavizumab, MedImmune, Gaithersburg, Md.; see U.S. Patent Application Publication No. US20110158985) made in house based on the published sequence, were compared in RSV A Long strain (ATCC Number VR-26™) and RSV B Washington strain18537 strain (ATCC Number VR-1580™). The test samples were three-fold serially diluted in EMEM supplemented with 2% heat inactivated FBS, for eleven dilution points. The serially diluted samples were then mixed with equal volumes of EMEM supplemented with 2% heat inactivated FBS containing 100 pfu/well of RSV A or B strains. After incubation at 37° C. for 1 hr, 100 μl of HEp-2 cells at a concentration of 1.5×10⁵ cells/ml was transferred to the 96 well plates containing the virus/antibody mixture. At 3 days post infection, the cells were washed once with PBS and then fixed in 80% acetone for 10 min at room temperature. A mixture of RSV F (mAb143-F3-B138) and RSV N (34C9) specific mouse mAbs (mAb143-F3-B138 and 34C9 are in house antibodies derived by immunizing mice with the respective antigens and immortalization of B-cells using the hybridoma technology) was added to the plates and incubated for 1 hour at room temperature. Plates were washed with PBS/0.05% Tween 20 and biotinylated horse anti-mouse IgG was added to the plates and incubated for 1 hour at room temperature. Plates were washed with PBS/0.05% Tween. Infrared dye-Streptavidin was used to detect RSV specific signal and two cell stains for assay normalization were added to the 96-well plates and incubated for 1 hour in the dark. Following 1 hour incubation, the plates were washed, air dried for 20 minutes in the dark and read on the Licor Aerius® Automated Imaging System utilizing a 700 channel laser for cell normalization and an 800 channel laser for detection of RSV specific signal. 800/700 ratios and percent neutralization were calculated and IC50 values were determined by four parameter curve fit in GraphPad.

RB-1+YTE was able to neutralize the RSV-A and RSV-B strains with equal potency (IC50 of 5-10 ng/ml). See Table 6.

TABLE 6

Measurement of Neutralization and Affinity for RB1 + YTE to RSV pre-fusion F and post-fusion F

| Mab | $IC_{50}$ In vitro neutralization (ng/ml) | | Kinetic Constants (pre-fusion F) | | | Kinetic Constants (post-fusion F) | | |
|---|---|---|---|---|---|---|---|---|
| | RSV A | RSV B | $K_{on}$ (M⁻¹s⁻¹) | $K_{off}$ (s⁻¹) | $K_D$ (nM) | $K_{on}$ (M⁻¹s⁻¹) | $K_{off}$ (s⁻¹) | $K_D$ (nM) |
| RB-1 | 3 | 1.7 | $4.4 \times 10^6$ | $1.4 \times 10^{-4}$ | 0.031 | $2.2 \times 10^6$ | $9 \times 10^{-4}$ | 0.41 |
| RB-1 + YTE | 3.6 | 3.49 | $3.2 \times 10^6$ | $2.3 \times 10^{-4}$ | 0.071 | $1.4 \times 10^6$ | $7 \times 10^{-4}$ | 0.48 |

The introduction of the YTE mutations in the Fc portion of the RB1 did not alter the antibody's in vitro potency to neutralize RSV A and B strains. The in vitro neutralization potency for RSV A was 3 and 3.6 ng/ml for RB1 and RB1+YTE respectively. The potencies for in vitro neutralization for RSV B were 1.7 and 3.49 ng/m for RB1 and RB1+YTE respectively. The kinetic constants as measured by Biocore were similar for RB1 and RB1+YTE suggesting that introduction of YTE in the Fc region of the antibody did not alter its antigen binding properties.

A non-GLP (Good Laboratory Practice) pharmacokinetics study was conducted at New Iberia Research Center (UL Lafayette, La.). Eight biologics-naïve male rhesus monkeys were randomized and assigned to one of two study groups (n=4 per group). Each animal received a single intravenous (i.v.) dose of RB1+YTE) or Motavizumab-YTE at 10 mg/kg. Blood samples were drawn prior to dosing on day 0, at 0.5, 1, 3, 8 and 24 h after dosing, and at 1, 2, 3, 5, 7 and 10 days after dosing. An ECL-based immunoassays was used to quantify both RB1+YTE (Human×[RSV] mAb (RB1-YTE) IgG1/Kappa (CE)) and Motavizumab_YTE (Humanized×[RSV] mAb IgG1/Kappa) in rhesus monkey serum.

The assay used biotinylated mouse anti-human IgG kappa chain (BD Biosciences, San Jose, Calif.) as a capture reagent and sulfoTAG mouse anti-Human IgG Fc as a detection reagent (SouthernBiotech Birmingham, Ala.). The Lower Limit of Quantification (LLOQ) of the assay was determined to be 1.37 ng/ml with Minimum Required Dilution (MRD) of 20.

Figure 7:
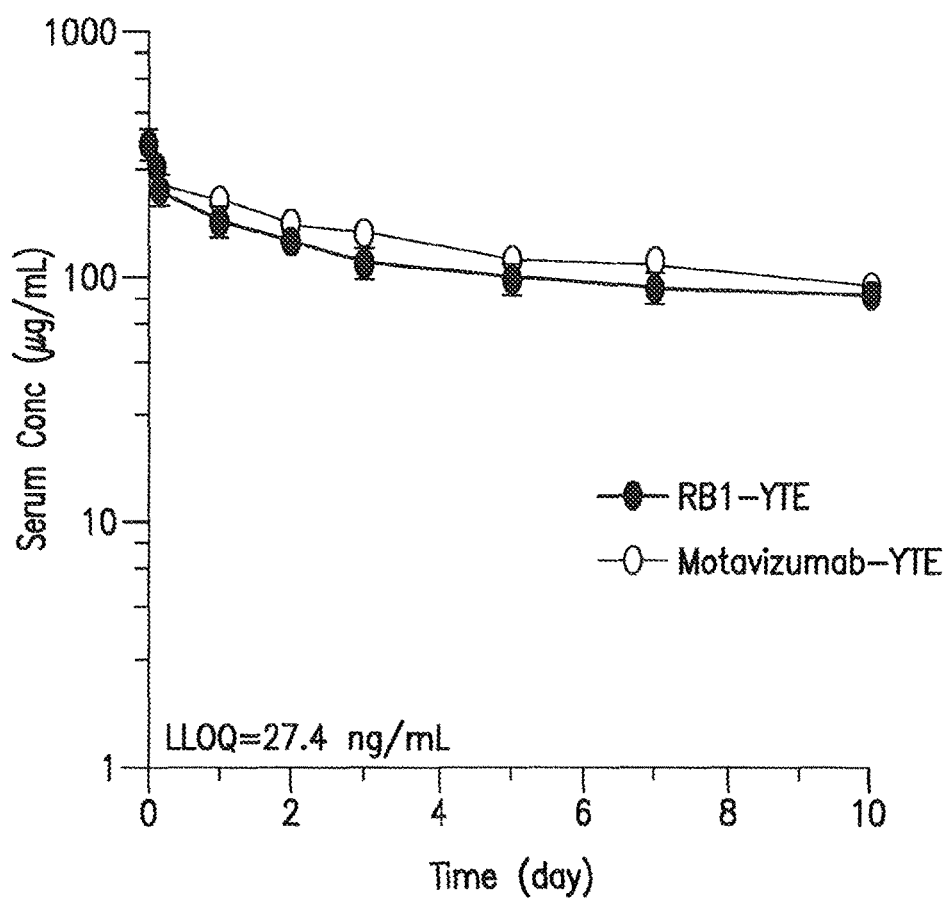
FIG. 7 shows pharmacokinetic properties in Rhesus of RB1-YTE (RB1+YTE) vs. motavizumab having the YTE mutation set.

Pharmacokinetics of RB1+YTE and Motavizumab-YTE were evaluated up to 10 days in rhesus macaque dosed intravenously at 10 mg/kg using the same immunoassay to quantify RB1+YTE and Motavizumab-YTE. For each animal, a non-compartmental model was fitted for the serum concentration data of each animal using Phoenix Winnonlin 6.3 (Certara, N.J.) to estimate the area under the curve (AUC0-10 day). AUC0-10 day was averaged across 4 animals for each treatment group and reported as mean±standard deviation. For RB1+YTE, AUC0-10 day=1159±116 µg/mL*day and for Motavizumab-YTE, AUC0-10 day=1381±63.0 µg/mL*day RB1+YTE (depicted as RB1-YTE in the figure legend) and Motavizumab-YTE showed similar serum concentration profiles and pharmacokinetics in rhesus macaque. See FIG. 7. RB1+YTE PK in NHP was also found to be comparable to motavizumab-YTE PK in cynomolgus monkey reported in literature. See Dall'Acqua et al., 2006, J Biol Chem, 281:23514-24.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 7

Sequence Information

| SEQ ID NO: | Description | SEQUENCE |
|---|---|---|
| 1 | RB1 H - CDR1 | DSAMS |
| 2 | RB1 H - CDR2 | FIKSKTYGGTKEYAASVKG |
| 3 | RB1 H - CDR3 | GAPYGGNSDYYYGLDV |
| 4 | RB1 L - CDR1 | RTSQDVRGALA |
| 5 | RB1 L - CDR2 | DASSLET |
| 6 | RB1 L - CDR3 | QQFLDFPFT |
| 7 | RB1 VH | EVQLVESGGGLVRPGRSLRLSCTVSGFSFDDSAMSWVRQAPGKGLEWISFIKSKTYGGTKEYAASVKGRFTISRDDSKNIAYLQMNSLKTEDTAVYYCTRGAPYGGNSDYYYGLDVWGQGTTVTVSS |
| 8 | RB1 VL (patient isolated) | DIQMTQSPSSLSASVGDRVTITCRTSQDVRGALAWYQQKPGKAPKLLIFDASSLETGVPSRFSGSGSGTVFTLTISSLQPEDFAAYYCQQFLDFPFTFGQGTRLEIKRT |
| 9 | RB1 VH (patient isolated) | EVQLVESGGGLVRPGRSLRLSCTVSGFSFDDSAMSWVRQAPGKGLEWISFIKSKTYGGTKEYAASVKGRFTISRDDSKNIAYLQMNSLKTEDTAVYYCTRGAPYGGNSDYYYGLDVWGQGTTVIVSS |
| 10 | Leader sequence | MGWSCIILFLVATATGVHS |
| 11 | RB1 VH + leader | MGWSCIILFLVATATGVHSEVQLVESGGGLVRPGRSLRLSCTVSGFSFDDSAMSWVRQAPGKGLEWISFIKSKTYGGTKEYAASVKGRFTISRDDSKNIAYLQMNSLKTEDTAVYYCTRGAPYGGNSDYYYGLDVWGQGTTVTVSS |
| 12 | RB1 VL + leader | MGWSCIILFLVATATGVHSDIQMTQSPSSLSASVGDRVTITCRTSQDVRGALAWYQQKPGKAPKLLIFDASSLETGVPSRFSGSGSGTVFTLTISSLQPEDFAAYYCQQFLDFPFTFGQGTRLEIKRT |
| 13 | Heavy chain constant domain-IgG1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCK |

TABLE 7-continued

Sequence Information

| SEQ ID NO: | Description | SEQUENCE |
|---|---|---|
| | | VSNKALPAPIEKTISKAKGQPREPQVYTLPPSRDELTKNQV SLTCLVKGFYPSDIAVEWESNGQPENNYKTTPPVLDSDGSF FLYSKLTVDKSRWQQGNVFSCSVMHEALHNHYTQKSLSLSP GK |
| 14 | Kappa light chain constant domain | VAAPSVFIFPPSDEQLKSGTASVVCLLNNFYPREAKVQWKV DNALQSGNSQESVTEQDSKDSTYSLSSTLTLSKADYEKHKV YACEVTHQGLSSPVTKSFNRGEC |
| 15 | Nucleic acid encoding RB1 VH | GAGGTGCAGCTGGTGGAGTCTGGGGGAGGCTTGGTACGGCC AGGGCGGTCCCTGAGACTCTCCTGCACAGTTTCTGGATTCA GCTTTGACGACTCTGCTATGAGCTGGGTCCGCCAGGCTCCA GGGAAGGGGCTGGAATGGATAAGTTTCATTAAAAGTAAAAC TTATGGTGGGACAAAAGAATACGCCGCGTCTGTGAAAGGCA GGTTCACCATCTCAAGAGATGATTCCAAAAACATCGCCTAT CTGCAAATGAACAGCCTGAAAACCGAGGACACAGCCGTGTA TTATTGTACTAGAGGGGCGCCTTACGGCGGTAACTCCGATT ACTACTACGGTTTGGACGTCTGGGGCCAAGGGACCACGGTC ACTGTCTCCTCA |
| 16 | Nucleic acid encoding RB1 VL | GACATCCAGATGACCCAGTCTCCATCCTCCCTGTCTGCATC TGTAGGAGACAGAGTCACCATCACTTGCCGGACAAGTCAGG ACGTTAGAGGTGCTTTAGCCTGGTATCAACAGAAACCAGGG AAAGCTCCTAAACTCCTGATCTTTGATGCCTCCAGTTTGGA GACTGGGGTCCCATCAAGGTTCAGCGGCAGTGGATCTGGGA CAGTTTTCACTCTCACCATCAGCAGCCTGCAGCCTGAAGAT TTTGCAGCTTATTACTGTCAGCAGTTTCTTGATTTCCCTTT CACCTTCGGCCAGGGGACACGACTGGAAATCAAACGTACG |
| 17 | Nucleic acid encoding RB1 VH (codon optimized) | GAGGTGCAGCTGGTCGAGAGCGGGGGGGGGCTGGTGCGGCC TGGCAGGTCTCTGAGACTGAGCTGCACCGTGAGCGGCTTCT CCTTTGACGATTCTGCCATGAGCTGGGTGCGGCAGGCTCCA GGCAAGGGACTGGAGTGGATCTCCTTCATCAAGTCTAAGAC CTACGCCGGCACAAAGGAGTACGCCGCTTCCGTGAAGGGCC GGTTTACCATCAGCAGGGACGATTCCAAGAACATCGCCTAT CTGCAGATGAACAGCCTGAAGACCGAGGACACAGCCGTGTA CTATTGCACAAGAGGAGCTCCTTACGGAGGCAACAGCGACT ACTATTACGGACTGGACGTGTGGGGACAGGGAACCACAGTG ACCGTGAGCTCC |
| 18 | Nucleic acid encoding RB1 VL (codon optimized) | GACATTCAGATGACTCAGTCCCCTTCAAGTCTGAGCGCCTC CGTGGGCGACAGAGTGACCATCACATGCCGGACCAGCCAGG ATGTGCGGGGCGCCCTGGCTTGGTACCAGCAGAAGCCAGGC AAGGCCCCCAAGCTGCTGATCTTTGACGCTAGCTCCCTGGA GACCGGCGTGCCCTCCAGGTTTTCTGGCAGCGGCTCCGGCA CAGTGTTCACCCTGACAATCTCTAGCCTGCAGCCTGAGGAC TTTGCCGCTTACTATTGCCAGCAGTTCCTGGATTTCCCCTT CACCTTCGGCCAAGGCACACGGCTGGAGATCAAGAGGACC |
| 19 | Nucleic acid encoding Leader sequence heavy chain | ATGGGTTGGTCCTGTATTATCCTGTTCCTGGTCGCCACTGC TACTGGGGTCCACTCA |
| 20 | Nucleic acid encoding Leader sequence light chain | ATGGGCTGGTCCTGTATTATCCTGTTCCTGGTGGCAACCGC AACTGGTGTGCATAGC |
| 21 | Nucleic acid encoding Heavy chain constant domain- IgG1 | GCCTCTACAAAGGGCCCTAGCGTGTTCCCACTGGCTCCCTC TTCCAAGTCTACCAGCGGAGGAACAGCCGCTCTGGGATGTC TGGTGAAGGATTACTTCCCAGAGCCCGTGACCGTGTCCTGG AACTCTGGCGCCCTGACCAGCGGAGTGCACACATTTCCAGC TGTGCTGCAGTCCTCTGGCCTGTATTCCCTGAGCTCCGTGG TGACCGTGCCCTCTAGCTCCCTGGGCACCCAGACATACATC TGTAACGTGAATCACAAGCCAAGCAATACAAAGGTGGACAA GAAGGTCGAGCCCAAGTCCTGTGATAAGACCCACACATGCC CCCCTTGTCCTGCTCCAGAGCTGCTGGGAGGACCTAGCGTG TTCCTGTTTCCACCCAAGCCTAAGGACACCCTGATGATCTC TAGGACCCCCGAGGTGACATGCGTGGTGGTGGACGTGAGCC ACGAGGATCCTGAGGTGAAGTTTAACTGGTACGTCGATGGC GTGGAGGTGCACAATGCCAAGACAAAGCCCAGAGAGGAGCA GTATAACTCCACCTACCGGGTGGTGTCTGTGCTGACAGTGC TGCACCAGGACTGGCTGAACGGCAAGGAGTACAAGTGCAAG GTGTCCAATAAGGCCCTGCCCGCTCCTATCGAGAAGACCAT CTCTAAGGCCAAGGGCCAGCCTAGGGAGCCACAGGTGTATA |

TABLE 7-continued

Sequence Information

| SEQ ID NO: | Description | SEQUENCE |
|---|---|---|
| | | CACTGCCTCCATCCAGAGACGAGCTGACCAAGAACCAGGTG TCTCTGACATGTCTGGTGAAGGGCTTCTACCCTTCTGATAT CGCCGTGGAGTGGGAGAGCAATGGCCAGCCAGAGAACAATT ATAAGACCACACCCCTGTGCTGGACAGCGATGGCTCCTTC TTTCTGTACAGCAAGCTGACCGTGGATAAGTCCCGGTGGCA GCAGGGCAACGTGTTCAGCTGTTCTGTGATGCACGAAGCCC TGCACAATCACTACACTCAGAAGAGCCTGTCCCTGTCACCT GGTAAA |
| 22 | Nucleic acid encoding Kappa light chain constant domain | GTGGCCGCTCCCTCCGTGTTTATCTTCCCCCCTTCTGACGA GCAGCTGAAGTCTGGCACAGCTAGCGTGGTGTGCCTGCTGA ACAATTTCTACCCTCGGGAGGCCAAGGTGCAGTGGAAGGTG GATAACGCTCTGCAGTCTGGCAATAGCCAGGAGTCCGTGAC CGAGCAGGACTCTAAGGATAGCACATATTCCCTGTCCTCTA CCCTGACACTGTCTAAGGCCGATTACGAGAAGCACAAGGTG TATGCTTGTGAAGTCACCCACCAGGGGCTGAGTTCACCAGT CACCAAGTCATTCAATCGGGGCGAGTGC |
| 23 | RB1 + YTE Heavy Chain | EVQLVESGGGLVRPGRSLRLSCTVSGFSFDDSAMSWVRQAP GKGLEWISFIKSKTYGGTKEYAASVKGRFTISRDDSKNIAY LQMNSLKTEDTAVYYCTRGAPYGGNSDYYYGLDVWGQGTTV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPELLG GPSVFLFPPKPKDTLYITREPEVTCVVVDVSHEDPEVKFNW YVDGVEVHNAKTKPREEQYNSTYRVVSVLTVLHQDWLNGKE YKCKVSNKALPAPIEKTISKAKGQPREPQVYTLPPSRDELT KNQVSLTCLVKGFYPSDIAVEWESNGQPENNYKTTPPVLDS DGSFFLYSKLTVDKSRWQQGNVFSCSVMHEALHNHYTQKSL SLSPGK |
| 24 | Nucleic acid encoding RB1 + YTE Heavy Chain (codon optimized) | GAGGTGCAGCTGGTGGAATCCGGCGGCGGACTGGTCAGACC TGGCAGATCCCTGAGGCTCAGCTGTACCGTGAGCGGCTTCA GCTTCGACGACTCCGCCATGAGCTGGGTGAGACAGGCCCCT GGCAAGGGCCTGGAGTGGATCAGCTTCATCAAGAGCAAAAC CTATGGCGGAACCAAGGAATACGCCGCCTCCGTGAAGGGCA GGTTCACCATTTCCAGGGACGACAGCAAGAACATCGCTTAC CTCCAGATGAACTCCCTCAAGACCGAGGATACCGCCGTGTA TTATTGCACCAGAGGCGCCCCCTACGGCGGCAATTCCGACT ATTACTACGGCCTGGATGTCTGGGGCCAAGGCACAACAGTG ACCGTGAGCTCCGCTAGCACCAAGGGACCCAGCGTGTTCCC CCTGGCCCCCAGCAGCAAGAGCACAAGCGGAGGAACAGCCG CCCTCGGCTGTCTGGTGAAAGACTACTTCCCCGAGCCTGTG ACAGTCAGCTGGAATAGCGGCGCTCTGACCAGCGGCGTCCA CACCTTTCCCGCTGTCCTGCAGAGCTCCGGCCTGTACAGCC TGTCCTCCGTGGTCACAGTGCCCTCCTCCAGCCTGGGCACA CAAACCTACATCTGTAACGTGAACCACAAGCCCAGCAACAC CAAGGTGGACAAGAAGGTCGAACCCAAATCCTGTGACAAGA CCCACACATGCCCCCCCTGCCCCGCCCCTGAGCTGCTGGGC GGCCCTTCCGTGTTCCTGTTCCCTCCCAAGCCCAAGGATAC CCTGTATATCACCAGAGAACCCGAGGTGACCTGTGTGGTGG TCGACGTCAGCCACGAAGATCCTGAGGTCAAGTTCAACTGG TATGTGGACGGCGTGGAGGTGCATAACGCCAAAACCAAGCC CAGGGAGGAACAGTATAACAGCACCTACAGGGTGGTGTCCG TCCTGACCGTGCTGCACCAGGACTGGCTGAACGGAAAGGAG TACAAATGTAAGGTCAGCAACAAAGCCCTGCCCGCTCCTAT CGAAAAGACCATCTCCAAGGCCAAAGGCCAGCCCAGAGAAC CCCAGGTGTACACCCTGCCCCCCTAGCAGAGACGAGCTGACC AAAAACCAGGTCTCCCTGACCTGCCTGGTGAAAGGCTTCTA CCCCAGCGATATCGCCGTGGAATGGGAAAGCAACGGCCAGC CTGAGAACAACTACAAGACCACCCCTCCCGTGCTCGACAGC GATGGCAGCTTCTTTCTGTACAGCAAGCTGACCGTGGACAA GAGCAGGTGGCAACAAGGCAACGTGTTCTCCTGCTCCGTGA TGCACGAGGCTCTGCACAACCACTATACCCAGAAGTCCCTG AGCCTCAGCCCCGGAAAATGA |
| 25 | RB1 + YTE Light Chain | DIQMTQSPSSLSASVGDRVTITCRTSQDVRGALAWYQQKPG KAPKLLIFDASSLETGVPSRFSGSGSGTVFTLTISSLQPED FAAYYCQQFLDFPPTFGQGTRLEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| 26 | Nucleic acid encoding RB1 + YTE Light Chain | GACATTCAGATGACTCAGTCCCCTTCAAGTCTGAGCGCCTC CGTGGGCGACAGAGTGACCATCACATGCCGGACCAGCCAGG ATGTGCGGGGCGCCCTGGCTTGGTACCAGCAGAAGCCAGGC |

TABLE 7-continued

| Sequence Information | |
|---|---|
| SEQ ID NO: Description | SEQUENCE |
| | AAGGCCCCCAAGCTGCTGATCTTTGACGCTAGCTCCCTGGA |
| | GACCGGCGTGCCCTCCAGGTTTTCTGGCAGCGGCTCCGGCA |
| | CAGTGTTCACCCTGACAATCTCTAGCCTGCAGCCTGAGGAC |
| | TTTGCCGCTTACTATTGCCAGCAGTTCCTGGATTTCCCCTT |
| | CACCTTCGGCCAAGGCACACGGCTGGAGATCAAGAGGACCG |
| | TGGCCGCTCCCTCCGTGTTTATCTTCCCCCCTTCTGACGAG |
| | CAGCTGAAGTCTGGCACAGCTAGCGTGGTGTGCCTGCTGAA |
| | CAATTTCTACCCTCGGGAGGCCAAGGTGCAGTGGAAGGTGG |
| | ATAACGCTCTGCAGTCTGGCAATAGCCAGGAGTCCGTGACC |
| | GAGCAGGACTCTAAGGATAGCACATATTCCCTGTCCTCTAC |
| | CCTGACACTGTCTAAGGCCGATTACGAGAAGCACAAGGTGT |
| | ATGCTTGTGAAGTCACCCACCAGGGGCTGAGTTCACCAGTC |
| | ACCAAGTCATTCAATCGGGGCGAGTGC |

The invention claimed is:

1. A method of preventing or treating an RSV infection in a human subject, comprising administering to the subject an effective amount of an antibody or antigen binding fragment that binds to human RSV F protein, wherein the antibody or antigen binding fragment comprises a heavy chain variable region CDR1 comprising the amino acid sequence of SEQ ID NO:1, a heavy chain variable region CDR2 comprising the amino acid sequence of SEQ ID NO:2, a heavy chain variable region CDR3 comprising the amino acid sequence of SEQ ID NO:3, a light chain variable region CDR1 comprising the amino acid sequence of SEQ ID NO:4, a light chain variable region CDR2 comprising the amino acid sequence of SEQ ID NO:5, and a light chain variable region CDR3 comprising the amino acid sequence of SEQ ID NO:6.

2. A method of preventing or treating transplantation related RSV infections in a human subject, comprising administering to the subject an effective amount of an antibody or antigen binding fragment that binds to human RSV F protein, wherein the antibody or antigen binding fragment comprises a heavy chain variable region CDR1 comprising the amino acid sequence of SEQ ID NO:1, a heavy chain variable region CDR2 comprising the amino acid sequence of SEQ ID NO:2, a heavy chain variable region CDR3 comprising the amino acid sequence of SEQ ID NO:3, a light chain variable region CDR1 comprising the amino acid sequence of SEQ ID NO:4, a light chain variable region CDR2 comprising the amino acid sequence of SEQ ID NO:5, and a light chain variable region CDR3 comprising the amino acid sequence of SEQ ID NO:6.

3. The method of claim 1, wherein the antibody or antigen binding fragment comprises a heavy chain variable domain having the amino acid sequence of SEQ ID NO:8 and a light chain variable domain having the amino acid sequence of SEQ ID NO:9.

4. The method of claim 1, wherein the antibody comprises a heavy chain having the amino acid sequence of SEQ ID NO:23 and a light chain having the amino acid sequence of SEQ ID NO:25.

5. The method of claim 1, wherein the method further includes administering to the subject an antibody or an antigen binding fragment thereof against a respiratory pathogen selected from influenza, human cytomegalovirus (hCMV), human metapneumovirus (hMPV), human parainfluenza (hPIV), human rhinovirus (hRV), mycoplasma pneumonia, streptococcus pneumoniae, adenovirus, bocavirus, enterovirus, norovirus, or BK virus.

6. The method of claim 5, wherein the respiratory pathogen is influenza, hCMV, hMPV, hPIV, norovirus, or BK virus.

7. The method of claim 1, wherein the antibody or antigen binding fragment that binds to human RSV F protein is provided in an immunogenic composition comprising an antigen selected from RSV F protein and RSV G protein and fragments thereof.

8. The method of claim 1, wherein the human subject is a human infant.

9. The method of claim 2, wherein the antibody or antigen binding fragment comprises a heavy chain variable domain having the amino acid sequence of SEQ ID NO:8 and a light chain variable domain having the amino acid sequence of SEQ ID NO:9.

10. The method of claim 2, wherein the antibody comprises a heavy chain having the amino acid sequence of SEQ ID NO:23 and a light chain having the amino acid sequence of SEQ ID NO:25.

11. The method of claim 2, wherein the method further includes administering to the subject an antibody or an antigen binding fragment thereof against a respiratory pathogen selected from influenza, human cytomegalovirus (hCMV), human metapneumovirus (hMPV), human parainfluenza (hPIV), human rhinovirus (hRV), mycoplasma pneumonia, streptococcus pneumoniae, adenovirus, bocavirus, enterovirus, norovirus, or BK virus.

12. The method of claim 11, wherein the respiratory pathogen is influenza, hCMV, hMPV, hPIV, norovirus, or BK virus.

13. The method of claim 2, wherein the antibody or antigen binding fragment that binds to human RSV F protein is provided in an immunogenic composition comprising an antigen selected from RSV F protein and RSV G protein and fragments thereof.

* * * * *

SEQUENCE LISTING

<160> NUMBER OF SEQ ID NOS: 26

<210> SEQ ID NO 1
<211> LENGTH: 5
<212> TYPE: PRT
<213> ORGANISM: Homo sapiens
<400> SEQUENCE: 1

Asp Ser Ala Met Ser
1               5

<210> SEQ ID NO 2
<211> LENGTH: 19
<212> TYPE: PRT
<213> ORGANISM: Homo sapiens
<400> SEQUENCE: 2

Phe Ile Lys Ser Lys Thr Tyr Gly Gly Thr Lys Glu Tyr Ala Ala Ser
1               5                   10                  15

Val Lys Gly

<210> SEQ ID NO 3
<211> LENGTH: 16
<212> TYPE: PRT
<213> ORGANISM: Homo sapiens
<400> SEQUENCE: 3

Gly Ala Pro Tyr Gly Gly Asn Ser Asp Tyr Tyr Tyr Gly Leu Asp Val
1               5                   10                  15

<210> SEQ ID NO 4
<211> LENGTH: 11
<212> TYPE: PRT
<213> ORGANISM: Homo sapiens
<400> SEQUENCE: 4

Arg Thr Ser Gln Asp Val Arg Gly Ala Leu Ala
1               5                   10

<210> SEQ ID NO 5
<211> LENGTH: 7
<212> TYPE: PRT
<213> ORGANISM: Homo sapiens
<400> SEQUENCE: 5

```
Asp Ala Ser Ser Leu Glu Thr
1               5

<210> SEQ ID NO 6
<211> LENGTH: 9
<212> TYPE: PRT
<213> ORGANISM: Homo sapiens

<400> SEQUENCE: 6

Gln Gln Phe Leu Asp Phe Pro Phe Thr
1               5

<210> SEQ ID NO 7
<211> LENGTH: 127
<212> TYPE: PRT
<213> ORGANISM: Artificial Sequence
<220> FEATURE:
<223> OTHER INFORMATION: RB-1 heavy chain with amino acid substitution

<400> SEQUENCE: 7

Glu Val Gln Leu Val Glu Ser Gly Gly Gly Leu Val Arg Pro Gly Arg
1               5                  10                  15

Ser Leu Arg Leu Ser Cys Thr Val Ser Gly Phe Ser Phe Asp Asp Ser
                20                  25                  30

Ala Met Ser Trp Val Arg Gln Ala Pro Gly Lys Gly Leu Glu Trp Ile
            35                  40                  45

Ser Phe Ile Lys Ser Lys Thr Tyr Gly Gly Thr Lys Glu Tyr Ala Ala
        50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr Val Ser Ser
        115                 120                 125

<210> SEQ ID NO 8
<211> LENGTH: 109
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Val Arg Gly Ala
                20                  25                  30

Leu Ala Trp Tyr Gln Gln Lys Pro Gly Lys Ala Pro Lys Leu Leu Ile
            35                  40                  45

Phe Asp Ala Ser Ser Leu Glu Thr Gly Val Pro Ser Arg Phe Ser Gly
        50                  55                  60

Ser Gly Ser Gly Thr Val Phe Thr Leu Thr Ile Ser Ser Leu Gln Pro
65                  70                  75                  80

Glu Asp Phe Ala Ala Tyr Tyr Cys Gln Gln Phe Leu Asp Phe Pro Phe
                85                  90                  95

Thr Phe Gly Gln Gly Thr Arg Leu Glu Ile Lys Arg Thr
            100                 105

<210> SEQ ID NO 9
```

```
<211> LENGTH: 127
<212> TYPE: PRT
<213> ORGANISM: Homo sapiens

<400> SEQUENCE: 9

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
            20                  25                  30

Ala Met Ser Trp Val Arg Gln Ala Pro Gly Lys Gly Leu Glu Trp Ile
        35                  40                  45

Ser Phe Ile Lys Ser Lys Thr Tyr Gly Gly Thr Lys Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Tyr Tyr Tyr
            100                 105                 110

Gly Leu Asp Val Trp Gly Gln Gly Thr Thr Val Ile Val Ser Ser
        115                 120                 125

<210> SEQ ID NO 10
<211> LENGTH: 19
<212> TYPE: PRT
<213> ORGANISM: Artificial Sequence
<220> FEATURE:
<223> OTHER INFORMATION: Leader sequence

<400> SEQUENCE: 10

Met Gly Trp Ser Cys Ile Ile Leu Phe Leu Val Ala Thr Ala Thr Gly
1               5                   10                  15

Val His Ser

<210> SEQ ID NO 11
<211> LENGTH: 146
<212> TYPE: PRT
<213> ORGANISM: Artificial Sequence
<220> FEATURE:
<223> OTHER INFORMATION: RBI VH amino acid substituted with leader

<400> SEQUENCE: 11

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Arg
            20                  25                  30

Pro Gly Arg Ser Leu Arg Leu Ser Cys Thr Val Ser Gly Phe Ser Phe
        35                  40                  45

Asp Asp Ser Ala Met Ser Trp Val Arg Gln Ala Pro Gly Lys Gly Leu
    50                  55                  60

Glu Trp Ile Ser Phe Ile Lys Ser Lys Thr Tyr Gly Gly Thr Lys Glu
65                  70                  75                  80

Tyr Ala Ala Ser Val Lys Gly Arg Phe Thr Ile Ser Arg Asp Asp Ser
                85                  90                  95

Lys Asn Ile Ala Tyr Leu Gln Met Asn Ser Leu Lys Thr Glu Asp Thr
            100                 105                 110

Ala Val Tyr Tyr Cys Thr Arg Gly Ala Pro Tyr Gly Gly Asn Ser Asp
        115                 120                 125
```

```
Tyr Tyr Tyr Gly Leu Asp Val Trp Gly Gln Gly Thr Thr Val Thr Val
            130                 135                 140

Ser Ser
145
```

<210> SEQ ID NO 12
<211> LENGTH: 128
<212> TYPE: PRT
<213> ORGANISM: Artificial Sequence
<220> FEATURE:
<223> OTHER INFORMATION: RB-1 VL and leader

<400> SEQUENCE: 12

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Asp Val
        35                  40                  45

Arg Gly Ala Leu Ala Trp Tyr Gln Gln Lys Pro Gly Lys Ala Pro Lys
    50                  55                  60

Leu Leu Ile Phe Asp Ala Ser Ser Leu Glu Thr Gly Val Pro Ser Arg
65                  70                  75                  80

Phe Ser Gly Ser Gly Ser Gly Thr Val Phe Thr Leu Thr Ile Ser Ser
                85                  90                  95

Leu Gln Pro Glu Asp Phe Ala Ala Tyr Tyr Cys Gln Gln Phe Leu Asp
            100                 105                 110

Phe Pro Phe Thr Phe Gly Gln Gly Thr Arg Leu Glu Ile Lys Arg Thr
        115                 120                 125
```

<210> SEQ ID NO 13
<211> LENGTH: 330
<212> TYPE: PRT
<213> ORGANISM: Homo sapiens

<400> SEQUENCE: 13

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

-continued

```
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 14
<211> LENGTH: 105
<212> TYPE: PRT
<213> ORGANISM: Homo sapiens

<400> SEQUENCE: 14

Val Ala Ala Pro Ser Val Phe Ile Phe Pro Pro Ser Asp Glu Gln Leu
1               5                   10                  15
Lys Ser Gly Thr Ala Ser Val Val Cys Leu Leu Asn Asn Phe Tyr Pro
            20                  25                  30
Arg Glu Ala Lys Val Gln Trp Lys Val Asp Asn Ala Leu Gln Ser Gly
        35                  40                  45
Asn Ser Gln Glu Ser Val Thr Glu Gln Asp Ser Lys Asp Ser Thr Tyr
    50                  55                  60
Ser Leu Ser Ser Thr Leu Thr Leu Ser Lys Ala Asp Tyr Glu Lys His
65                  70                  75                  80
Lys Val Tyr Ala Cys Glu Val Thr His Gln Gly Leu Ser Ser Pro Val
                85                  90                  95
Thr Lys Ser Phe Asn Arg Gly Glu Cys
            100                 105

<210> SEQ ID NO 15
<211> LENGTH: 381
<212> TYPE: DNA
<213> ORGANISM: Artificial Sequence
<220> FEATURE:
<223> OTHER INFORMATION: RB-1 with amino acid substitution

<400> SEQUENCE: 15
gaggtgcagc tggtggagtc tgggggaggc ttggtacggc cagggcggtc cctgagactc    60
tcctgcacag tttctggatt cagctttgac gactctgcta tgagctgggt ccgccaggct   120
ccagggaagg ggctggaatg gataagtttc attaaaagta aaacttatgg tgggacaaaa   180
gaatacgccg cgtctgtgaa aggcaggttc accatctcaa gagatgattc caaaaacatc   240
```

```
gcctatctgc aaatgaacag cctgaaaacc gaggacacag ccgtgtatta ttgtactaga    300
ggggcgcctt acggcggtaa ctccgattac tactacggtt tggacgtctg gggccaaggg    360
accacggtca ctgtctcctc a                                              381
```

<210> SEQ ID NO 16
<211> LENGTH: 327
<212> TYPE: DNA
<213> ORGANISM: Homo sapiens

<400> SEQUENCE: 16

```
gacatccaga tgacccagtc tccatcctcc ctgtctgcat ctgtaggaga cagagtcacc     60
atcacttgcc ggacaagtca ggacgttaga ggtgctttag cctggtatca acagaaacca    120
gggaaagctc ctaaactcct gatctttgat gcctccagtt tggagactgg ggtcccatca    180
aggttcagcg gcagtggatc tgggacagtt ttcactctca ccatcagcag cctgcagcct    240
gaagattttg cagcttatta ctgtcagcag tttcttgatt tccctttcac cttcggccag    300
gggacacgac tggaaatcaa acgtacg                                        327
```

<210> SEQ ID NO 17
<211> LENGTH: 381
<212> TYPE: DNA
<213> ORGANISM: Artificial Sequence
<220> FEATURE:
<223> OTHER INFORMATION: RB-1 VH codon optimized

<400> SEQUENCE: 17

```
gaggtgcagc tggtcgagag cggggggggg ctggtgcggc tggcaggtc tctgagactg     60 agctgcaccg tgagcggctt ctcctttgac gattctgcca tgagctgggt gcggcaggct    120
ccaggcaagg gactggagtg gatctccttc atcaagtcta agacctacgg cgcacaaag    180 gagtacgccg cttccgtgaa gggccggttt accatcagca ggacgattc aagaacatc    240 gcctatctgc agatgaacag cctgaagacc gaggacacag ccgtgtacta ttgcacaaga    300
ggagctcctt acggaggcaa cagcgactac tattacggac tggacgtgtg gggacaggga    360
accacagtga ccgtgagctc c                                              381
```

<210> SEQ ID NO 18
<211> LENGTH: 327
<212> TYPE: DNA
<213> ORGANISM: Artificial Sequence
<220> FEATURE:
<223> OTHER INFORMATION: RB-1 VL codon optimized

<400> SEQUENCE: 18

```
gacattcaga tgactcagtc ccctccaagt ctgagcgcct ccgtgggcga cagagtgacc     60
atcacatgcc ggaccagcca ggatgtgcgg ggcgccctgg cttggtacca gcagaagcca    120
ggcaaggccc ccaagctgct gatctttgac gctagctccc tggagaccgg cgtgccctcc    180
aggttttctg gcagcggctc cggcacagtg ttcaccctga caatctctag cctgcagcct    240
gaggactttg ccgcttacta ttgccagcag ttcctggatt tcccccttcac cttcggccaa    300 ggcacacggc tggagatcaa gaggacc                                        327
```

<210> SEQ ID NO 19
<211> LENGTH: 57
<212> TYPE: DNA
<213> ORGANISM: Artificial Sequence
<220> FEATURE:
<223> OTHER INFORMATION: Leader sequence heavy chain

<400> SEQUENCE: 19
atgggttggt cctgtattat cctgttcctg gtcgccactg ctactggggt ccactca    57

<210> SEQ ID NO 20
<211> LENGTH: 57
<212> TYPE: DNA
<213> ORGANISM: Artificial Sequence
<220> FEATURE:
<223> OTHER INFORMATION: Leader sequence light chain

<400> SEQUENCE: 20
atgggctggt cctgtattat cctgttcctg gtggcaaccg caactggtgt gcatagc    57

<210> SEQ ID NO 21
<211> LENGTH: 990
<212> TYPE: DNA
<213> ORGANISM: Homo sapiens

<400> SEQUENCE: 21
gcctctacaa agggccctag cgtgttccca ctggctccct cttccaagtc taccagcgga    60
ggaacagccg ctctgggatg tctggtgaag gattacttcc cagagcccgt gaccgtgtcc    120
tggaactctg gcgccctgac cagcggagtg cacacatttc agctgtgct gcagtcctct    180 ggcctgtatt ccctgagctc cgtggtgacc gtgccctcta gctccctggg cacccagaca    240
tacatctgta acgtgaatca caagccaagc aatacaaagg tggacaagaa ggtcgagccc    300
aagtcctgtg ataagaccca cacatgcccc ccttgtcctg ctccagagct gctgggagga    360
cctagcgtgt tcctgttttcc acccaagcct aaggacaccc tgatgatctc taggaccccc    420
gaggtgacat gcgtggtggt ggacgtgagc cacgaggatc ctgaggtgaa gtttaactgg    480
tacgtcgatg gcgtggaggt gcacaatgcc aagacaaagc cagagagga gcagtataac    540 tccacctacc gggtggtgtc tgtgctgaca gtgctgcacc aggactggct gaacggcaag    600
gagtacaagt gcaaggtgtc caataaggcc ctgcccgctc tatcgagaa gaccatctct    660 aaggccaagg gccagcctag ggagccacag gtgtatacac tgcctccatc cagagacgag    720
ctgaccaaga accaggtgtc tctgacatgt ctggtgaagg gcttctaccc ttctgatatc    780
gccgtggagt gggagagcaa tggccagcca gagaacaatt ataagaccac accccctgtg    840
ctggacagcg atggctcctt ctttctgtac agcaagctga ccgtggataa gtcccggtgg    900
cagcagggca acgtgttcag ctgttctgtg atgcacgaag ccctgcacaa tcactacact    960
cagaagagcc tgtccctgtc acctggtaaa    990

<210> SEQ ID NO 22
<211> LENGTH: 315
<212> TYPE: DNA
<213> ORGANISM: Homo sapiens

<400> SEQUENCE: 22
gtggccgctc cctccgtgtt tatcttcccc ccttctgacg agcagctgaa gtctggcaca    60
gctagcgtgg tgtgcctgct gaacaatttc taccctcggg aggccaaggt gcagtggaag    120
gtggataacg ctctgcagtc tggcaatagc caggagtccg tgaccgagca ggactctaag    180
gatagcacat attccctgtc ctctaccctg acactgtcta aggccgatta cgagaagcac    240
aaggtgtatg cttgtgaagt cacccaccag gggctgagtt caccagtcac caagtcattc    300
aatcggggcg agtgc    315

```
<210> SEQ ID NO 23
<211> LENGTH: 457
<212> TYPE: PRT
<213> ORGANISM: Artificial Sequence
<220> FEATURE:
<223> OTHER INFORMATION: RB1+YTE HEAVY CHAIN

<400> SEQUENCE: 23

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
            20                  25                  30

Ala Met Ser Trp Val Arg Gln Ala Pro Gly Lys Gly Leu Glu Trp Ile
        35                  40                  45

Ser Phe Ile Lys Ser Lys Thr Tyr Gly Gly Thr Lys Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Tyr Ile Thr Arg Glu Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365
```

```
Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
450                 455

<210> SEQ ID NO 24
<211> LENGTH: 1374
<212> TYPE: DNA
<213> ORGANISM: Artificial Sequence
<220> FEATURE:
<223> OTHER INFORMATION: NUCLEIC ACID ENCODING RB1+YTE HEAVY CHAIN
      (CODON OPTIMIZED)

<400> SEQUENCE: 24
gaggtgcagc tggtggaatc cggcggcgga ctggtcagac tggcagatcc cctgaggctc      60
agctgtaccg tgagcggctt cagcttcgac gactccgcca tgagctgggt gagacaggcc    120
cctggcaagg gcctggagtg gatcagcttc atcaagagca aaacctatgg cggaaccaag    180
gaatacgccg cctccgtgaa gggcaggttc accatttcca gggacgacag caagaacatc    240
gcttacctcc agatgaactc cctcaagacc gaggataccg ccgtgtatta ttgcaccaga    300 ggcgcccct acggcggcaa ttccgactat tactacggcc tggatgtctg gggccaaggc    360
acaacagtga ccgtgagctc cgctagcacc aagggaccca gcgtgttccc cctggccccc    420
agcagcaaga gcacaagcgg aggaacagcc gccctcggct gtctggtgaa agactacttc    480
cccgagcctg tgacagtcag ctggaatagc ggcgctctga ccagcggcgt ccacaccttt    540
cccgctgtcc tgcagagctc cggcctgtac agcctgtcct ccgtggtcac agtgccctcc    600
tccagcctgg gcacacaaac ctacatctgt aacgtgaacc acaagcccag caacaccaag    660
gtggacaaga aggtcgaacc caaatccctg acaagaccc acacatgccc ccctgccc    720 gcccctgagc tgctgggcgg cccttccgtg ttcctgttcc ctcccaagcc caaggatacc    780
ctgtatatca ccagagaacc cgaggtgacc tgtgtggtgg tcgacgtcag ccacgaagat    840
cctgaggtca agttcaactg gtatgtggac ggcgtggagg tgcataacgc aaaaccaag    900 cccagggagg aacagtataa cagcacctac agggtggtgt ccgtcctgac cgtgctgcac    960
caggactggc tgaacggaaa ggagtacaaa tgtaaggtca gcaacaaagc cctgcccgct   1020
cctatcgaaa agaccatctc caaggccaaa ggccagccca gagaaccca ggtgtacacc    1080 ctgccccta gcagagacga gctgaccaaa aaccaggtct ccctgacctg cctggtgaaa   1140
ggcttctacc ccagcgatat cgccgtggaa tgggaaagca acggccagcc tgagaacaac   1200
tacaagacca cccctcccgt gctcgacagc gatggcagct ctttctgta cagcaagctg   1260 accgtggaca gagcaggtg gcaacaaggc aacgtgttct cctgctccgt gatgcacgag   1320
gctctgcaca accactatac ccagaagtcc ctgagcctca gccccggaaa atga         1374

<210> SEQ ID NO 25
<211> LENGTH: 214
<212> TYPE: PRT
```

<213> ORGANISM: Artificial Sequence
<220> FEATURE:
<223> OTHER INFORMATION: RB1+YTE LIGHT CHAIN

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Val Arg Gly Ala
            20                  25                  30

Leu Ala Trp Tyr Gln Gln Lys Pro Gly Lys Ala Pro Lys Leu Leu Ile
        35                  40                  45

Phe Asp Ala Ser Ser Leu Glu Thr Gly Val Pro Ser Arg Phe Ser Gly
50                  55                  60

Ser Gly Ser Gly Thr Val Phe Thr Leu Thr Ile Ser Ser Leu Gln Pro
65                  70                  75                  80

Glu Asp Phe Ala Ala Tyr Tyr Cys Gln Gln Phe Leu Asp Phe Pro Phe
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 642
<212> TYPE: DNA
<213> ORGANISM: Artificial Sequence
<220> FEATURE:
<223> OTHER INFORMATION: NUCLEIC ACID ENCODING RB1+YTE LIGHT CHAIN

<400> SEQUENCE: 26

```
gacattcaga tgactcagtc cccttcaagt ctgagcgcct ccgtgggcga cagagtgacc      60
atcacatgcc ggaccagcca ggatgtgcgg ggcgccctgg cttggtacca gcagaagcca     120
ggcaaggccc ccaagctgct gatctttgac gctagctccc tggagaccgg cgtgccctcc     180
aggttttctg gcagcggctc cggcacagtg ttcaccctga caatctctag cctgcagcct     240
gaggactttg ccgcttacta ttgccagcag ttcctggatt tccccttcac cttcggccaa     300
ggcacacggc tggagatcaa gaggaccgtg gccgctccct ccgtgtttat cttccccct      360 tctgacgagc agctgaagtc tggcacagct agcgtggtgt gcctgctgaa caatttctac     420
cctcgggagg ccaaggtgca gtggaaggtg ataacgctc tgcagtctgg caatagccag     480
gagtccgtga ccgagcagga ctctaaggat agcacatatt ccctgtcctc taccctgaca     540
```

```
ctgtctaagg ccgattacga gaagcacaag gtgtatgctt gtgaagtcac ccaccagggg      600
ctgagttcac cagtcaccaa gtcattcaat cggggcgagt gc                         642
```